(12) United States Patent
Boyer et al.

(10) Patent No.: US 7,018,985 B1
(45) Date of Patent: Mar. 28, 2006

(54) COMPOSITION AND METHOD FOR INHIBITING PLATELET AGGREGATION

(75) Inventors: José L. Boyer, Chapel Hill, NC (US); Gillian M. Olins, Cary, NC (US); Benjamin R. Yerxa, Raleigh, NC (US); James G. Douglass, III, Apex, NC (US)

(73) Assignees: Inspire Pharmaceuticals, Inc., Durham, NC (US); University of North Carolina at Chapel Hill, Chapel Hill, NC (US)

( * ) Notice: Subject to any disclaimer, the term of this patent is extended or adjusted under 35 U.S.C. 154(b) by 283 days.

(21) Appl. No.: 09/643,138

(22) Filed: Aug. 21, 2000

(51) Int. Cl.
*A61K 31/70* (2006.01)
*C07H 19/20* (2006.01)

(52) U.S. Cl. ............. 514/48; 536/26.2; 536/26.23; 536/26.26; 514/45; 514/46; 514/47; 514/50; 514/51

(58) Field of Classification Search ........... 514/45, 514/46, 47, 48, 49, 50, 51, 81; 536/26.2, 536/26.23, 26.26; 544/264, 265
See application file for complete search history.

(56) References Cited

U.S. PATENT DOCUMENTS

| | | |
|---|---|---|
| 4,621,076 A | 11/1986 | Kuzuya et al. |
| 5,049,550 A | 9/1991 | Zamecnik ............... 514/47 |
| 5,292,498 A | 3/1994 | Boucher ................. 424/45 |
| 5,596,088 A | 1/1997 | Boucher et al. ........ 536/23.5 |
| 5,607,836 A | 3/1997 | Boucher et al. ........ 435/7.2 |
| 5,628,984 A | 5/1997 | Boucher ................. 424/45 |
| 5,635,160 A | 6/1997 | Stutts et al. ............ 424/45 |
| 5,654,285 A | 8/1997 | Ingall et al. ............ 514/47 |
| 5,656,256 A | 8/1997 | Boucher et al. ........ 424/45 |
| 5,681,823 A | 10/1997 | Kim et al. .............. 514/47 |
| 5,691,156 A | 11/1997 | Boucher et al. ........ 435/7.21 |
| 5,721,219 A | 2/1998 | Ingall et al. ............ 514/47 |
| 5,747,496 A | 5/1998 | Cox et al. .............. 514/258 |
| 5,763,447 A | 6/1998 | Jacobus et al. ......... 514/265 |
| 5,789,391 A | 8/1998 | Jacobus et al. ......... 514/51 |
| 5,837,861 A | 11/1998 | Pendergast et al. ..... 536/25.6 |
| 5,900,407 A | 5/1999 | Yerxa et al. ........... 514/47 |
| 5,902,567 A | 5/1999 | Boucher ................. 424/9.1 |
| 5,935,555 A | 8/1999 | Stutts et al. ............ 424/45 |
| 5,955,447 A | 9/1999 | Ingall et al. ............ 514/47 |
| 5,958,897 A | 9/1999 | Jacobus et al. ......... 514/49 |
| 5,962,432 A | 10/1999 | LaCroix et al. ........ 514/47 |
| 5,968,913 A | 10/1999 | LaCroix et al. ........ 514/47 |
| 5,972,904 A | 10/1999 | Jacobus et al. ......... 514/47 |
| 5,981,506 A | 11/1999 | Jacobus et al. ......... 514/47 |
| 6,022,527 A | 2/2000 | Boucher et al. ........ 424/45 |
| 6,037,343 A | 3/2000 | Ali ........................ 514/252 |
| 6,040,317 A | 3/2000 | Duggan et al. ......... 514/317 |
| 6,133,247 A | 10/2000 | Boucher et al. ........ 514/50 |
| 6,143,279 A | 11/2000 | Boucher et al. ........ 424/45 |
| 6,159,952 A | 12/2000 | Shaffer et al. .......... 514/47 |
| 6,166,022 A | 12/2000 | Brown et al. .......... 514/258 |
| 6,323,187 B1 * | 11/2001 | Yerxa et al. ........... 514/51 |
| 6,528,640 B1 | 3/2003 | Beigelman |

FOREIGN PATENT DOCUMENTS

| | | |
|---|---|---|
| GB | 1407903 | 10/1995 |
| WO | WO 89/04321 | 5/1989 |
| WO | WO 92/01673 | 7/1991 |
| WO | WO 92/17488 | 10/1992 |
| WO | WO 94/08593 | 4/1994 |
| WO | WO 94/18216 | 8/1994 |
| WO | WO 95/10538 | 4/1995 |
| WO | WO 97/03084 | 1/1997 |
| WO | WO 97/29456 | 8/1997 |
| WO | WO 97/35591 | 10/1997 |
| WO | WO 98/03177 | 1/1998 |
| WO | WO 98/03182 | 1/1998 |
| WO | WO 98/15835 | 4/1998 |
| WO | WO 98/19685 | 5/1998 |
| WO | WO 98/28300 | 7/1998 |
| WO | WO 98/34593 | 8/1998 |
| WO | WO 98/34942 | 8/1998 |
| WO | WO 99/01138 | 1/1999 |
| WO | WO 99/05155 | 2/1999 |
| WO | WO 99/09998 | 3/1999 |
| WO | WO 99/32085 | 7/1999 |
| WO | WO 99/61012 | 12/1999 |
| WO | WO 00/30629 | 6/2000 |
| WO | WO 00/33080 | 6/2000 |
| WO | WO 00/34283 | 6/2000 |
| WO | WO 00/39145 | 7/2000 |
| WO | WO 00/50024 | 8/2000 |
| WO | WO 01/19826 | 3/2001 |
| WO | WO 01/36421 | 5/2001 |
| WO | WO 01/39781 | 6/2001 |
| WO | PCT/US01/41818 | 3/2002 |

OTHER PUBLICATIONS

Kim et al., J. Biol. Chem. vol. 269(9), pp. 6471–6477, 1994.*

Neuhaus, K. L. et al., "Safety Observations from the Piolet Phase of the Randomized r–Hirudin for Improvement of Thrombolysis (HIT–III) Study," *Circulation* 90(4): 1638–1642 (1994).

(Continued)

*Primary Examiner*—James O. Wilson
*Assistant Examiner*—Howard V. Owens
(74) *Attorney, Agent, or Firm*—Howrey LLP; Viola T. Kung

(57) ABSTRACT

The present invention provides novel compounds of dinucleotide polyphosphates and the method of preventing or treating diseases or conditions associated with platelet aggregation. The method comprises administering systemically to a patient a pharmaceutical comprising a purinergic $P2_T$ receptor antagonist, in an amount effective to elevate its extracellular concentration to bind to $P2_T$ receptors and inhibit $P2_T$ receptor-mediated platelet aggregation. Methods of systemic administration include injection by intravenous, intramuscular, intrasternal and intravitreal routes, infusion, transdermal administration, oral administration, rectal administration and intra-operative instillation.

38 Claims, No Drawings

OTHER PUBLICATIONS

Olivier, K. et al., "Acute Safety and Effects on Mucociliary Clearance of Aerosolized Uridine 5'—Triphosphate + Amiloride in Normal Human Adults,"–*Am. J. Respir. Crit. Care Med.*154:217–223 (1996).

Quinn, M and Desmond J. Fitzgerald, "Ticlopidine and Clopidogrel," *Circulation*100(15):1667–1672 (1999).

Romson, J., et al., "Electrical Induction of Coronary Artery Thrombosis in the Ambulatory Canine: A model for IN VIVO Evaluation of Anti–Throbotic Agents," *Thromb. Res.*17:841–853 (1980).

Shebuski, R., et al., "Acceleration of Recombinant Tissue–Type Plasminogen Activator–Induced Thrombolysis and Prevention of Reocclusin by the Combination of Heparin and the Arg–Gly–Asp–Containing Peptide Bitistatin in a Canie Model of Coronary Thrombosis," *Circulation*82(1):169–177 (1990).

Tschopp, J.F., et al., "Inhibition of coronary artery reocclusion after thrombolysis with an RGD–containing peptide with no significant effect on bleeding time," *Coron. Artery Dis.*4:809–817 (1993).

Weber, M., et al., "Low–Dose Verses for Prevention of Coronary Graft Occlusion,"Anticoagulans *Am. J. Cardiol.*66:1461–1468 (1990).

Bernat, A., et al., "Effect of Various Antiplatelet Agents on the Acute Arterial Thrombosis in the Rat," *Thromb. Haemostas*. (1993) 70(5)812–816.

Bush, L., et al., "Effects of the selective thromboxane synthetase inhibitor dazoxiben on variations in cyclic blood flow in stenosed canie coronary arteries," *Circulation*69(5):1161–1170, (1984).

EPIC Investigators, "Use of a Monoclonal Antibody Directed against the Platelet Glycoprotein lib/iiia Receptor in High–Risk Coronary Angioplasty," *New England J. Med.*(1994) 330:956–961.

Folts, J. et al., "Platelet Aggregation in Partially Obstructed Vessels and its Elimination with Asprian," *Circulation*54(3): 365–370 (1976).

Frederick, L.G., et al., "The Protective Dose of the Potent GPIIb/IIIa Antagonist SC–54701A is Reduced When Used in Combination with Asprian and Heparin in Canie Model of Coronary Artery Thrombosis," *Circulation*93(1): 129–134 (1996).

Geiger, J., et al., "Specific impairment of Human Platelet P2Y ac ADP Receptor–Mediated Signaling by the Antiplatelet Drug Clopidogrel," *Arterioscler. Thromb. Vasc. Biol.*19:2007–2011.

Gusto lia Investigators, The Global Use of Strategies to Open Occluded Coronary Arties., "Randomized Trial of Intravenous Heprain Versus Recombinant Hirudin for Acute Coronary Syndromes", *Circulation*90(4):1631–1637 (1994).

Hass, W. et al., "A Randomized Trial Comparing Ticlopidine Hydrochloride with Asprian for the Prevention of Stroke for High–Risk Patients," *N. Engl. J. Med.*321(8):501–507 (1989).

Herbert, J.M. et al., Inhibitory Effect of Clopidogrel on Platelet Adhesion and Intimal Proliferation After Arterial Injury in Rabbits, *Arterioscl. Thromb.*(1993) 13(8):1171–1179.

Hourani, et al., The Platelet ADP Receptors Meeting, La Thuile, Italy, Mar. 29–31, 2000.

Humphries, R.G. et al., "Pharmacological profile of the novel P25–Purinoceptor antagonist, FPL 67085 in vitro and in the anaesthesized rat in vitro," *Br. J. Pharmacol.*115:1110–1116 (1995).

Ingall, A., et al., "Antagonists of the Platelet P2t Receptor: A Novel Approach to Antithrombotic Therapy," *J. Med. Chem.*42:213–220 (1999).

Lazarowski, E., et al., "Pharmacological selectivity of the cloned human P2u–purinoceptor: potent activation by diadenosine tetraphosphate," *Brit. J. Pharm.*116:1619–1627 (1995).

Lekstkrom, J and William R. Bell, "Asprian in the Prevention of Thrombosis," *Medicine*70(3):161–178 (1991).

Maffrand, J.P., et al., "ADP Plays a Key Role in Thrombogenesis in Rats," *Thromb. Haemostas.*(1988) 59(2):225–230.

Mickelson, J.K. et al., "Antiplatelet Antibody [7E3 F(ab')2] Prevents Rethrombosis After Recombinant Tissue–Type Plasminogen Activator–Induced Coronary Artery Thrombolysis in a canie Model," *Circulation*81(2):617–627 (1990).

Antiplatelet Trialists'Collaboration., "Collaborative overview of randomised trials of antiplatelet therapy–I: Prevention of Death, myocardial infarction, and stroke by prolonged antiplatelet therapy in various categories of patients," *Br. Med. J.*308: 81–106 (1994).

Antiplatelet Trialists'Collaboration., "Collaborative overview of randomised trials of antiplatelet–therapy–II: Maintenance of Vascular graft or arterial patency by antiplatelet therapy," *Br. Med. J.*308: 159–168 (1994.

Antman, E, for the TIMI 9a Investigatiors, "Hirudin in Acute Myocardial Infarction,", *Circulation*, 90(4):1624–1630 (1994).

U.S. Appl. No. 09/934,970, filed Oct. 20, 2004, Boyer et al.

Hamilton, A. et al., "Design of Substrate–Site–Directed Inhibitors of Adenylate Kinase and Hexokinase. Effect of Substrate Substituents on Affinity for the Adenine Nucleotide Sites", *J. Med. Chem.*, 19:1371–1377 (1976).

Hiratsuka T., "Affinity Labeling of the Myosin ATPase with Ribose–Modified Fluorescent Nucleotides and Vanadate", *J. Biochem.*, 96:147–154 (1984).

Martin, P. et al., "Structure–Activity Studies of Analogs of $\beta_1\gamma$–Methylene–ATP at $P_{2x}$–Purinoceptors in the Rabbit Ear Central Artery", *Drug Development Research*, 36: 153–165 (1995).

Metzker, M. et al., "Termination of DNA synthesis by novel3'–modified–deoxyribonucleoside 5'–triphophate", *Nucleic Acids Research*, 22:4259–4267 (1994).

Pelicano, H. et al., "Study of the substrate–binding properties of bovine liver adenosine kinase and inhibition by fluorescent nucleoside analogues", *Eur. J. Biochem.*, 248:930–937 (1997).

Richard, J. and Frey, P.A., "Stereochemical Course of Thiophosphoryl Group Transfer Catalyzed by Adenylate Kinase", *J. Am. Chem. Soc.*, 100:7757–7758 (1978).

Sekine, M. et al., "New Type of Chemical Oxidative Phosphorylation: Activation of Phosphonate Function by Use of Triisopropylbenzenesulfonyl Chloride", *Tetrahedron Letters*, 1145–1148 (1997).

Zatorski, A. et al., "Chemical Synthesis of Benzamide Adenine Dinucleotide: Inhibition of Inosine Monophosphate Dehydrogenase (Types I and II)", *Journal of Medicinal Chemistry, American Chemical Society*, 39:2422–2426 (1996).

Alessi, D. et al., "Synthesis and Properties of a Conformationally Restricted Spin–Labeled Analog of ATP and Its Interaction with Myosin and Skeletal Muscle" *Biochemistry* (1992), 31(34), 8043–54.

Bujalowski, W. et al., "Structural Characteristics of the Nucleotide–Binding Site of *Escherichia coli* Primary Replicative Helicase DnaB Protein. Studies with Ribose and Base–Modified Fluorescent Nucleotide Analogs" *Biochemistry* (1994), 33(15), 4682–94.

Cardullo, R. A. et al., "Synthesis, Purification, and Characterization of 2,4,6–Trinitrophenyl–UDP–galactose: A Fluorescent Substrate for Galactosyltransferase" *Analytical Biochemistry* (1990), 188(2), 305–9.

Carvalho–Alves, P. et al., "Stoichiometric Photolabeling of Two Distinct Low and High Affinity Nucleotide Sites in Sarcoplasmic Reticulum ATPase" *Journal of Biological Chemistry* (1985), 260(7), 4282–7.

Chapal, J. et al., "Comparative effect of adenosine–5'–triphosphate and related analogs on insulin secretion from the rat pancreas" *Fundamental & Clinical Pharmacology* (1997), 11(6), 537–545.

Hiratsuka, Toshiaki, "Biological Activities and Spectroscopic Properties of Chromophoric and Fluorescent Analogs of Adenine Nucleoside and Nucleotides, 2',3'–O–(2,4, 6–Trinitrocyclohexadienylidene) Adenosine Derivatives" *Biochimica et Biophysica Acta* (1982), 719(3), 509–17.

Hiratsuka, Toshiaki, "Monitoring the Myosin ATPase Reaction Using a Sensitive Fluorescent Probe: Pyrene–Labeled ATP" *Biophysical Journal* (1997), 72(2, Pt. 1), 843–849.

Ikehara, M. et al., "III. Interaction Between Synthetic Adenosine Triphosphate Analogs and Actomyosin Systems" *Biochimica et Biophysica Acta* (1965), 100(2), 471–8.

Ikehara, M. et al., "Unusual Rapid Cleavage of Terminal Phosphate Group of N6–Disubstituted Adenosine 5'–Triphosphate (ATP)by Divalent Cation" *Biochimica et Biophysica Acta* (1964), 85(3), 512–515.

Kwiatkowski, A. et al., "Mapping of the Adenosine 5'–Triphosphate Binding Site of Type II Calmodulin–Dependent Protein Kinase" *Biochemistry* (1987), 26(24), 7636–40.

Lowe, G. et al., "Evidence of a Dissociative $S_N1(P)$ Mechanism of Phosphoryl Transfer by Rabbit Muscle Pyruvate Kinase" *Journal of the Chemical Society, Perkin Transactions 1: Organic and Bio–Organic Chemistry (1972–1999)* (1978), (12), 1622–30.

Marian, M., "Acetyl Derivatives of Nucleoside 5'–Triphosphates. I." *Microchemical Journal* (1984), 29(2), 219–27.

Mayer, I. et al., "Interaction of Fluorescent Adenine Nucleotide Derivatives with the ADP/ATP Carrier in Mitochondria. 1. Comparison of Various 3'–O–Ester Adenine Nucleotide Derivatives" *Biochemistry* (1984), 23(11), 2436–42.

Murataliev, M. et al., "Interaction of mitochondrial $F_1$–ATPase with trinitrophenyl derivatives of ATP Photoaffinity labeling of binding sites with 2–azido–2',3'–O–(2,4, 6–trinitrophenyl)adenosine 5'–triphosphate" *European Journal of Biochemistry* (1995), 232(2), 578–85.

Oliveira, C. R. G. et al., "Interaction of Spin–Labeled Nucleotides with Sarcoplasmic Reticulum Adenosinetriphosphatase" *Biochemistry* (1988), 27(16), 5923–7.

Ray, S. et al., "Microenvironment at the Substrate Binding Subsite of the Active Site of UDPglucose 4–Epimerase from *Kluyveromyces Fragilis* Using a Fluorescent Analog of UMP" *Indian Journal of Biochemistry & Biophysics* (1992), 29(2), 209–13.

Seebregts, C. et al., "2',3'–O–(2,4, 6–Trinitrophenyl)–8–Azido–adenosine Mono–, Di–, and Triphosphates as Photoaffinity Probes of the $Ca^{2+}$–ATPase of Sarcoplasmic Reticulum. Regulatory/Superfluorescent Nucleotides Label the Catalytic Site with High Efficiency" *Journal of Biological Chemistry* (1989), 264(4), 2043–52.

Soslau, G. et al., "Aggregation of Human and Canine Platelets: Modulation by Purine Nucleotides" *Thrombosis Research* (1993), 72(2), 127–37.

Thoenges D. et al., "Tight Binding of Bulky Fluorescent Derivatives of Adenosine to The Low Affinity $E_2$ATP Site Leads to Inhibition of Na+/K+–ATPase. Analysis of Structural Requirements of Fluorescent ATP Derivatives with a Koshland–Nemethy–Filmer Model of Two Interacting ATP Sites" *Journal of Biological Chemistry* (Jan. 22, 1999), 274(4), 1971–8.

Vigne, P. et al., "Benzoyl ATP Is an Antagonist of Rat and Human $P2Y_1$ Receptors and of Platelet Aggregation" *Biochemical and Biophysical Research Communications* (1999), 256(1), 94–97.

Ward, D. et al., "Photoinactivation of Fluorescein Isothiocyanate–modified Na,K–ATPase by 2'(3')–O–(2,4, 6–Trinitrophenyl)8–azidoadenosine 5'–Diphosphate. Abolition of E1 and E2 Partial Reactions by Sequential Block of High and Low Affinity Nucleotide Sites" *Journal of Biological Chemistry* (1998), 273(23), 14277–14284.

\* cited by examiner

COMPOSITION AND METHOD FOR INHIBITING PLATELET AGGREGATION

TECHNICAL FIELD

This invention relates to compounds of mono and dinucleotide polyphosphates and the method of using such compounds in the prevention or treatment of diseases or conditions associated with platelet aggregation, including thrombosis in humans and other mammals.

BACKGROUND OF THE INVENTION

Hemostasis is the spontaneous process of stopping bleeding from damaged blood vessels. Precapillary vessels contract immediately when cut; within seconds, thrombocytes, or blood platelets, are bound to the exposed matrix of the injured vessel by a process called platelet adhesion. Platelets also stick to each other in a phenomenon known as platelet aggregation to form a platelet plug to stop bleeding quickly.

An intravascular thrombus results from a pathological disturbance of hemostasis. Platelet adhesion and aggregation are critical events in intravascular thrombosis. Activated under conditions of turbulent blood flow in diseased vessels or by the release of mediators from other circulating cells and damaged endothelial cells lining the vessel, platelets accumulate at a site of vessel injury and recruit further platelets into the developing thrombus. The thrombus can grow to sufficient size to block off arterial blood vessels. Thrombi can also form in areas of stasis or slow blood flow in veins. Venous thrombi can easily detach portions of themselves called emboli that travel through the circulatory system and can result in blockade of other vessels, such as pulmonary arteries. Thus, arterial thrombi cause serious disease by local blockade, whereas venous thrombi do so primarily by distant blockade, or embolization. These conditions include venous thrombosis, thrombophlebitis, arterial embolism, coronary and cerebral arterial thrombosis, unstable angina, myocardial infarction, stroke, cerebral embolism, kidney embolisms and pulmonary embolisms.

A number of converging pathways lead to platelet aggregation. Whatever the initial stimulus, the final common event is crosslinking of platelets by binding fibrinogen to a membrane binding site, glycoprotein IIb/IIIa (GPIIb/IIIa). Compounds that are antagonists for GPIIb/IIIa receptor complex have been shown to inhibit platelet aggregation (U.S. Pat. Nos. 6,037,343 and 6,040,317). Antibodies against GPIIb/IIIa have also been shown to have high antiplatelet efficacy (The EPIC investigators, *New Engl. J. Med.* (1994) 330:956-961). However, this class of antiplatelet agents sometimes causes bleeding problems.

Thrombin can produce platelet aggregation largely independently of other pathways but substantial quantities of thrombin are unlikely to be present without prior activation of platelets by other mechanisms. Thrombin inhibitors such as hirudin are highly effective antithrombotic agents. However, functioning as both antiplatelet and anti-coagulant agents, thrombin inhibitors again may produce excessive bleeding. (The TIMI 9 a investigators, The GUSTO IIa investigators, *Circulation*, 90: 1624-1630 (1994); *Circulation*, 90: 1631-1637 (1994); Neuhaus K. L. et al., *Circulation*, 90: 1638-1642 (1994))

Various antiplatelet agents have been studied for many years as potential targets for inhibiting thrombus formation. Some agents such as aspirin and dipyridamole have come into use as prophylactic antithrombotic agents, and others have been the subjects of clinical investigations. To date, the powerful agents such as disintegrins, and the thienopyridines ticlopidine and clopidogrel have been shown to have substantial side effects, while agents such as aspirin have useful but limited effectiveness (Hass, et al., N. Engl. J. Med., 321:501–507 (1989); Weber, et al., *Am. J. Cardiol.* 66:1461–1468 (1990); Lekstrom and Bell, *Medicine* 70:161–177 (1991)). In particular, use of the thienopyridines in antiplatelet therapy has been shown to increase the incidence of potentially life threatening thrombotic thrombocytopenic purpura (Bennett, C.L. et al. *N. Engl. J. Med,* (2000) 342: 1771–1777). Aspirin, which has a beneficial effect on platelet aggregation (*Br. Med. J.* (1994) 308: 81–106; 159–168), acts by inducing blockade of prostaglandin synthesis. Aspirin has no effect on ADP-induced platelet aggregation, and thus has limited effectiveness on platelet aggregation. Furthermore, its well documented high incidence of gastric side effects limits its usefulness in many patients. Clinical efficacy of some newer drugs, such as ReoPro (7E3), is impressive, but recent trials have found that these approaches are associated with an increased risk of major bleeding, sometimes necessitating blood transfusion (*New Engl. J. Med.* (1994) 330:956–961). Thus it appears that the ideal "benefit/risk" ratio has not been achieved.

Recent studies have suggested that adenosine 5'-diphosphate (ADP), a common agonist, plays a key role in the initiation and progression of arterial thrombus formation (Bernat, et al., *Thromb. Haemostas.* (1993) 70:812–826); Maffrand, et al., *Thromb. Haemostas.* (1988) 59:225–230; Herbert, et al., *Arterioscl. Thromb.* (1993) 13:1171–1179). ADP induces platelet aggregation, shape change, secretion, influx and intracellular mobilization of $Ca^{+2}$, and inhibition of adenylyl cyclase. Binding of ADP to platelet receptors is required for elicitation of the ADP-induced platelet responses. There are at least three P2 receptors expressed in human platelets: a cation channel receptor $P2X_1$, a G protein-coupled receptor $P2Y_1$, and a G protein-coupled receptor $P2Y_\tau$, (also referred to as $P2Y_{ac}$ and $P2Y_{12}$). The $P2X_1$ receptor is responsible for rapid calcium influx and is activated by ATP and by ADP. However, its direct role in the process of platelet aggregation is unclear. The $P2Y_1$ receptor is responsible for calcium mobilization, shape change and the initiation of aggregation. $P2Y_\tau$ receptor is responsible for inhibition of adenylyl cyclase and is required for full aggregation. (Hourani, et al., The Platelet ADP Receptors Meeting, La Thuile, Italy, Mar. 29–31, 2000)

Ingall et al. (*J. Med. Chem.* 42: 213–220, (1999)) describe a dose-related inhibition of ADP-induced platelet aggregation by analogues of adenosine triphosphate (ATP), which is a weak, nonselective but competitive $P2Y_\tau$ receptor antagonist. Zamecnik (USPN 5,049,550) discloses a method for inhibiting platelet aggregation in a mammal by administering to said mammal a diadenosine tetraphosphate compound of App(CH$_2$)ppA or its analogs. Kim et al. (USPN 5,681, 823) disclose $P^1$, $P^4$-dithio-$P^2$, $P^3$-monochloromethylene 5', 5" diadenosine $P^1$, $P^4$-tetraphosphate as an antithrombotic agent. The thienopyridines ticlopidine and clopidogrel, which are metabolized to antagonists of the platelet $P2Y_\tau$ receptor, are shown to inhibit platelet function in vivo (Quinn and Fitzgerald, *Circulation* 100:1667–1672 (1999);

Geiger, et al., *Arterioscler. Thromb. Vasc. Biol.* 19:2007-2011 (1999)).

There is a need in the area of cardiovascular and cerebrovascular therapeutics for an agent that can be used in the prevention and treatment of thrombi, with minimal side effects, such as unwanted prolongation of bleeding in other parts of the circulation, while preventing or treating target thrombi. The inventors of the present invention have discovered new compounds that are antagonists of the effect of ADP on its platelet membrane receptor, the $P2Y_\tau$ receptor. The compounds provide efficacy as antithrombotic agents by their ability to block ADP from acting at its platelet receptor site and thus prevent platelet aggregation. Thus, these new compounds can provide a more efficacious antithrombotic effect than aspirin, but with less profound effects on bleeding than antagonists of the fibrinogen receptor. Alternately, the compounds of the present invention can be used in conjunction with lower doses of these other agents which inhibit platelet aggregation by different mechanisms, to reduce the toxicity of these agents. Finally, if the compounds of the present invention have sufficient binding affinity and bear a fluorescent moiety, they can find uses as biochemical probes for the $P2_\tau$ receptor.

SUMMARY OF THE INVENTION

The invention provides molecules whose structures fall within general Formula I, and pharmaceutical formulations thereof. The invention also provides compounds useful for the prevention of thrombosis. Accordingly, a broad embodiment of the invention relates to compounds of general formula I, or salts thereof:

$Z'$=hydrogen or $OR_2$;
A=M, alkyl, cycloalkyl, aralkyl, aryl, or acylthioalkyl, with or without substituents or heteroatoms; or
A is a nucleoside residue which is defined as:

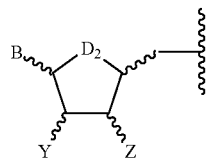

and which is linked to the phosphate chain via the 5' position of the furanose or carbocycle; wherein:
$D_2$=O or C;
Z=hydrogen or $OR_3$;
Y=hydrogen or $OR_4$;
B is a purine or a pyrimidine residue according to general formulas IV and V which is linked to the furanose or carbocycle via the 9- or 1-position, respectively;
$R_1$, $R_2$, $R_3$, and $R_4$ can be H, provided that at least one of the four is a residue according to general formulas II and III which is linked to the 2' or 3' furanose or carbocycle hydroxyl oxygen via a carbon atom.
When $D_1$ and $D_2$ are oxygen, the furanosyl moieties are in the D-configuration, but may be L-, or D- and L-. The D-configuration is preferred.

The invention also provides pharmaceutical compositions comprising compounds of Formula I, which are highly selective antagonists of $P_{2\tau}$ receptor on platelets. The invention further provides a method of preventing or treating

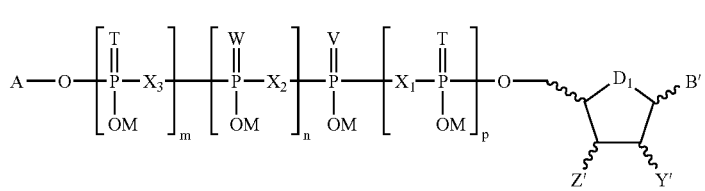

Formula I wherein:
$X_1$, $X_2$, and $X_3$ are independently or together oxygen, methylene, monochloromethylene, dichloromethylene, monofluoromethylene, difluoromethylene, or imido;
T, W, and V are independently to together oxygen or sulfur;
m=0,1 or 2;
n=0 or 1;
p=0,1, or 2;
where the sum of m+n+p is from 0 to 5;
M=hydrogen or a pharmaceutically-acceptable inorganic or organic counterion;
$D_1$=O or C;
B' is a purine or a pyrimidine residue according to general formulas IV and V which is linked to the 1' position of the furanose or carbocycle via the 9- or 1-position, respectively;
Y'=hydrogen or $OR_1$;

diseases or conditions associated with platelet aggregation; such diseases include venous thrombosis, thrombophlebitis, arterial embolism, coronary and cerebral arterial thrombosis, unstable angina, myocardial infarction, stroke, cerebral embolism, kidney embolisms and pulmonary embolisms. The method comprises administering to a patient a pharmaceutical composition comprising a compound of Formula I in an amount effective to bind to the $P_{2\tau}$ receptors on platelets and inhibit ADP-induced platelet aggregation.

DETAILED DESCRIPTION OF THE INVENTION

This invention provides molecules which fall within the scope of general Formula I, and pharmaceutically acceptable salts thereof. Accordingly, a broad embodiment of the invention relates to compounds of general formula I, or salts thereof:

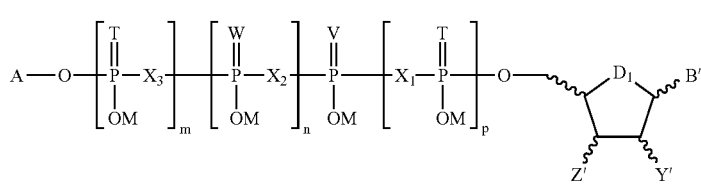

Formula I wherein:
$X_1$, $X_2$, and $X_3$ are independently or together oxygen, methylene, monochloromethylene, dichloromethylene, monofluoromethylene, difluoromethylene, or imido;
T, W, and V are independently or together oxygen or sulfur;
m=0, 1 or 2;
n=0 or 1;
p=0, 1, or 2;
where the sum of m+n+p is from 0 to 5;

Further provisions are that when $D_1$ and $D_2$ are oxygen, the furanose is preferably in the β-configuration;

and that the furanose is most preferably in the β-D-configuration.

Preferred compounds of general Formula I are molecules whose structures fall within the definitions of Formula Ia and Formula Ib:

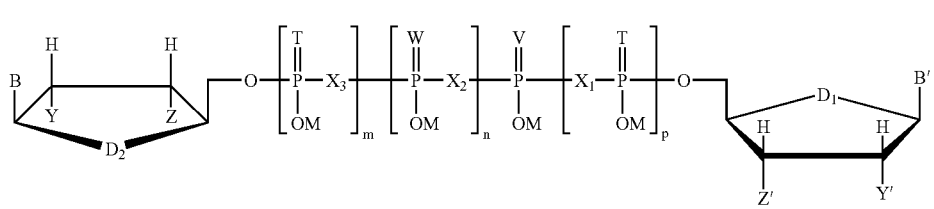

Formula Ia

M=H or a pharmaceutically-acceptable inorganic or organic counterion;
$D_1$=O or C;
B' is a purine or a pyrimidine residue according to general formulas IV and V which is linked to the 1' position of the furanose or carbocycle via the 9- or 1- position, respectively;
Y'=H or $OR_1$;
Z'=H or $OR_2$;
A=M, alkyl, cycloalkyl, aralkyl, aryl, or acylthioalkyl, with or without substituents or heteroatoms; or
A is a nucleoside residue which is defined as:

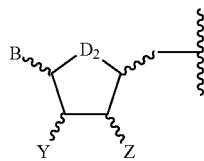

and which is linked to the phosphate chain via the 5' position of the furanose or carbocycle;
wherein:
Z=H or $OR_3$;
Y=H or $OR_4$;
$D_2$=O or C;
B is a purine or a pyrimidine residue according to general formulas IV and V which is linked to the sugar via the 9- or 1-position, respectively;
$R_1$, $R_2$, $R_3$, and $R_4$ can be H, provided that at least one of the four is a residue according to general formulas II and III which is linked to the 2' or 3' furanose or carbocycle hydroxyl oxygen via a carbon atom;

wherein:
$X_1$, $X_2$, and $X_3$=O;
T, V, and W=O;
M=H, $NH_4^{\pm}$, $Na^+$ or other pharmaceutically-acceptable inorganic or organic counterion;
Y'=H, OH, or $OR_1$, where $OR_1$ falls under the definition of general formula II;
Z'=OH or $OR_2$, where $OR_2$ falls under the definition of general formula II;
Z=OH or $OR_3$, where $OR_3$ falls under the definition of general formula II;
Y=H, OH, or $OR_4$, where $OR_4$ falls under the definition of general formula II;
$D_1$=O;
$D_2$=O or C;
B and B' are purine or pyrimidine residues according to general formulas IV and V;
m and p=0,1 or 2;
n=0 or 1;
such that the sum of m+n+p is from 0 to 5; or
$X_1$, $X_2$, and $X_3$=O;
T, V, and W=O;
M=H, $NH_4^{\pm}$, $Na^+$ or other pharmaceutically-acceptable inorganic or organic counterion;
Y'=H, OH, or $OR_1$, where $OR_1$ falls under the definition of general formula III;
Z'=OH or $OR_2$, where $OR_2$ falls under the definition of general formula III;
Z=OH or $OR_3$, where $OR_3$ falls under the definition of general formula III;
Y=H, OH, or $OR_4$, where $OR_4$ falls under the definition of general formula III;

$D_1=O$;
$D_2=O$ or C;
B and B' are purine or pyrimidine residues according to general formulas IV and V;
m and p=0,1 or 2;
n=0 or 1;
such that the sum of m=n=p is from 0 to 5; or
$X_1$ and $X_3=O$;
$X_2$ = methylene, monochloromethylene, dichloromethylene, monofluoromethylene, difluoromethylene, or imido;
T, V, and W=O;
M=H, $NH_4^\pm$, $Na^+$ or other pharmaceutically-acceptable inorganic or organic counterion;
Y'=H, OH, or $OR_1$, where $OR_1$ falls under the definition of general formula II;
Z'=OH or $OR_2$, where $OR_2$ falls under the definition of general formula II;
Z=OH or $OR_3$, where $OR_3$ falls under the definition of general formula II;
Y=H, OH, or $OR_4$, where $OR_4$ falls under the definition of general formula II;
$D_1=O$;
$D_2=O$ or C;
B and B' are purine or pyrimidine residues according to general formulas IV and V;
m and p=0,1 or 2;
n=1;
such that the sum of m=n=p is from 1 to 5; or
$X_1$ and $X_3=O$;
$X_2$ = methylene, monochloromethylene, dichloromethylene, monofluoromethylene, difluoromethylene, or imido;
T, V, and W=O;
M=H, $NH_4^\pm$, $Na^+$ or other pharmaceutically-acceptable inorganic or organic counterion;
Y'=H, OH, or $OR_1$, where $OR_1$ falls under the definition of general formula III;
Z'=OH or $OR_2$, where $OR_2$ falls under the definition of general formula III;
Z=OH or $OR_3$, where $OR_3$ falls under the definition of general formula III;
Y=H, OH, or $OR_4$, where $OR_4$ falls under the definition of general formula III;
$D_1=O$;
$D_2=O$ or C;
B and B' are purine or pyrimidine residues according to general formulas IV and V;
m and p=0,1 or 2;
n=1;
such that the sum of m+n+p is from 1 to 5; or
$X_1$ and $X_3=O$;
$X_2$ = methylene, monochloromethylene, dichloromethylene, monofluoromethylene, difluoromethylene, or imido;
T=S;
V and W=O;
M=H, $NH_4^\pm$, $Na^+$ or other pharmaceutically-acceptable inorganic or organic counterion;
Y'=H, OH, or $OR_1$, where $OR_1$ falls under the definition of general formula II;
Z'=OH or $OR_2$, where $OR_2$ falls under the definition of general formula II;
Z=OH or $OR_3$, where $OR_3$ falls under the definition of general formula II;
Y=H, OH, or $OR_4$, where $OR_4$ falls under the definition of general formula II;
$D_1=O$;
$D_2=O$ or C;
B and B' are purine or pyrimidine residues according to general formulas IV and V;
m, n, and p=1; or
$X_1$ and $X_3=O$;
$X_2$ = methylene, monochloromethylene, dichloromethylene, monofluoromethylene, difluoromethylene, or imido;
T=S;
V and W=O;
M=H, $NH_4^\pm$, $Na^+$ or other pharmaceutically-acceptable inorganic or organic counterion;
Y'=H, OH, or $OR_1$, where $OR_1$ falls under the definition of general formula III;
Z'=OH or $OR_2$, where $OR_2$ falls under the definition of general formula III;
Z=OH or $OR_3$, where $OR_3$ falls under the definition of general formula III;
Y=H, OH or $OR_4$, where $OR_4$ falls under the definition of general formula III;
$D_1=O$;
$D_2=O$ or C;
B and B' are purine or pyrimidine residues according to general formulas IV and V;
m, n, and p=1; or

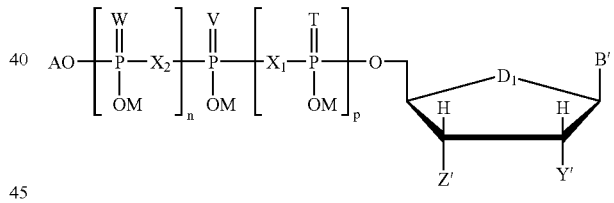

Formula Ib where for general formula I, m=0, and all other definitions remain the same;
wherein:
A=M, alkyl, cycloalkyl, aralkyl, aryl, or acylthioalkyl, with or without substituents or heteroatoms;
$X_1$ and $X_2=O$;
T, V, and W=O;
M=H, $NH_4^\pm$, $Na^+$ or other pharmaceutically-acceptable inorganic or organic counterion;
Y'=H, OH, or $OR_1$, where $OR_1$ falls under the definition of general formula II;
Z'=OH or $OR_2$, where $OR_2$ falls under the definition of general formula II;
With the provision that at least one of Y' and Z' is $OR_1$ or $OR_2$;
$D_1=O$ or C;
B' is purine or pyrimidine residue according to general formulas IV and V;
n and p=0,1, or 2 such that the sum of n+p is from 0 to 3; or A=M, alkyl, cycloalkyl, aralkyl, aryl, or acylthioalkyl, with or without substituents or heteroatoms;

$X_1$ and $X_2$=O;

T, V, and W=O;

M=H, $NH_4^\pm$, $Na^+$ or other pharmaceutically-acceptable inorganic or organic counterion;

Y'=$OR_1$, where $OR_1$ falls under the definition of general formula III;

Z'=$OR_2$, where $OR_2$ falls under the definition of general formula III;

$D_1$=O or C;

B' is purine or pyrimidine residue according to general formulas IV and V;

n and p=0,1, or 2 such that the sum of n=p is from 0 to 3; or

A=M, alkyl, cycloalkyl, aralkyl, aryl, or acylthioalkyl, with or without substituents or heteroatoms;

$X_1$ and $X_2$=O;

T and V=O;

W=S;

M=H, $NH_4^\pm$, $Na^+$ or other pharmaceutically-acceptable inorganic or organic counterion;

Y'=H, OH, or $OR_1$, where $OR_1$ falls under the definition of general formula II;

Z'=OH or $OR_2$, where $OR_2$ falls under the definition of general formula II;

With the provision that at least one of Y' and Z' is $OR_1$ or $OR_2$;

$D_1$=O or C;

B' is purine or pyrimidine residue according to general formulas IV and V;

p=0,1, or 2 such that the sum of n+p is from 1 to 3;

n=1; or

A=M, alkyl, cycloalkyl, aralkyl, aryl, or acylthioalkyl, with or without substituents or heteroatoms;

$X_1$ and $X_2$=O;

T and V=O;

W=S;

M=H, $NH_4^\pm$, $Na^+$ or other pharmaceutically-acceptable inorganic or organic counterion;

Y'=$OR_1$, where $OR_1$ falls under the definition of general formula III;

Z'=$OR_2$, where $OR_2$ falls under the definition of general formula III;

$D_1$=O or C;

B'is purine or pyrimidine residue according to general formulas IV and V;

p=0,1, or 2 such that the sum of n+p is from 1 to 3;

n=1; or

A=M, alkyl, cycloalkyl, aralkyl, aryl, or acylthioalkyl, with or without substituents or heteroatoms;

$X_1$=O;

$X_2$=methylene, monochloromethylene, dichloromethylene, monofluoromethylene, difluoromethylene, imido;

T, V, and W=O;

M=H, $NH_4^\pm$, $Na^+$ or other pharmaceutically-acceptable inorganic or organic counterion;

Y'=H, OH, or $OR_1$, where $OR_1$ falls under the definition of general formula II;

Z'=H, OH or $OR_2$, where $OR_2$ falls under the definition of general formula II;

With the provision that at least one of Y' and Z' is $OR_1$ or $OR_2$;

$D_1$=O or C;

B' is purine or pyrimidine residue according to general formulas IV and V;

p=0, 1, or 2 such that the sum of n+p is from 1 to 3;

n=1; or

A=M, alkyl, cycloalkyl, aralkyl, aryl, or acylthioalkyl, with or without substituents or heteroatoms;

$X_1$=O;

$X_2$=methylene, monochloromethylene, dichloromethylene, monofluoromethylene, difluoromethylene, or imido;

T, V, and W=O;

M=H, $NH_4^\pm$, $Na^+$ or other pharmaceutically-acceptable inorganic or organic counterion;

Y'=$OR_1$, where $OR_1$ falls under the definition of general formula III;

Z'=$OR_2$, where $OR_2$ falls under the definition of general formula III;

$D_1$=O or C;

B' is purine or pyrimidine residue according to general formulas IV and V;

p=0, 1, or 2 such that the sum of n+p is from 1 to 3;

n=1; or

For compounds according to formula Ia or Ib, where Y'=$OR_1$, Z'=$OR_2$, Z=$OR_3$ and/or Y=$OR_4$, at least one of the four must be a residue which is linked directly to the corresponding 2' or 3' hydroxyl oxygen of the furanose or carbocycle via a carbon atom. For the most part, this residue falls within the scope of formula II or formula III:

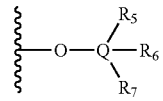

Formula II wherein:

O is the corresponding 2' and/or 3' oxygen of the furanose or carbocycle;

Q is a carbon atom;

$R_5$, $R_6$, and $R_7$ are H, an alkyl, cycloalkyl, aralkyl, aryl, substituted aralkyl, or substituted aryl, such that the moiety defined according to formula II is an ether; or provided that $R_5$ and $R_6$ are taken together to mean oxygen or sulfur doubly bonded to Q, and $R_7$ is alkyl, cycloalkyl, aralkyl, aryl, substituted aralkyl, or substituted aryl, such that the moiety defined according to formula II is an ester or thioester; or provided that $R_5$ and $R_6$ are taken together to mean oxygen or sulfur doubly bonded to Q, and $R_7$ is amino or mono- or disubstituted amino, where the substituents are alkyl, cycloalkyl, aralkyl, aryl, substituted aralkyl, or substituted aryl, such that the moiety according to formula II is a carbamate or thiocarbamate; or provided that $R_5$ and $R_6$ are taken together to mean oxygen or sulfur doubly bonded to Q, and $R_7$ is alkoxy, cycloalkoxy, aralkyloxy, aryloxy, substituted aralkyloxy, or substituted aryloxy, such that the moiety according to formula II is a carbonate or thiocarbonate; or provided that $R_5$ and $R_6$ are taken together to mean oxygen or sulfur doubly bonded to Q and both the 2' and 3' oxygens of the furanose are directly bound to Q to form a cyclical carbonate or thiocarbonate, $R_7$ is not present; or

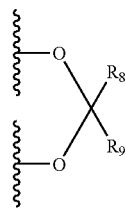

Formula III wherein:

O is the 2' and 3' oxygens of the furanose or carbocycle; and the 2' and 3' oxygens of the furanose or carbocycle are linked by a common carbon atom to form a cyclical acetal, cyclical ketal, or cyclical orthoester; and for cyclical acetals and ketals, $R_8$ and $R_9$ are independently hydrogen, alkyl, cycloalkyl, aralkyl, aryl, substituted aralkyl, substituted aryl, or may be joined together to form a homocyclic or heterocyclic ring composed of 3 to 8 atoms, or for cyclical orthoesters, $R_8$ is hydrogen, alkyl, cycloalkyl, aralkyl, aryl, substituted aralkyl, or substituted aryl, and $R_9$ is alkyloxy, cycloalkyloxy, aralkyloxy, aryloxy, substituted aralkyloxy, or substituted aryloxy.

In general, $R_5$ to $R_9$ may be defined as, but are not limited to, the following:

Alkyl groups are from 1 to 8 carbons, either straight chained or branched, with or without unsaturation and with or without heteroatoms;

Cycloalkyl groups are from 3 to 8 carbons, with or without unsaturation, and with or without heteroatoms;

Aralkyl groups are from 1 to 5 carbons in the alkyl portion, and are monocyclic or polycyclic moieties from 4 to 8 carbons per ring, with or without heteroatoms, in the aryl portion;

Aryl groups are monocyclic or polycyclic moieties from 4 to 8 carbons, with or without heteroatoms; and these groups may or may not bear substituents.

Preferred substituents on the foregoing groups may be, but are not limited to, hydroxy, nitro, methoxy, fluoro, chloro, bromo, iodo, methyl, ethyl, propyl, butyl, thioalkyl, alkoxy, carboxyl, cyano, amino, substituted amino, trifluoromethyl, phenyl, cyclopropyl, cyclopentyl, and cyclohexyl; and Preferred heteroatoms are oxygen, nitrogen, and sulfur.

B and B' are independently a purine residue, as in formula IV, linked through the 9-position, or a pyrimidine residue, as in formula V, linked through the 1-position. The ribosyl moieties are in the D-configuration, as shown, but may be L-, or D- and L-. The D-configuration is preferred.

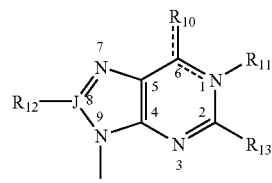

Formula IV

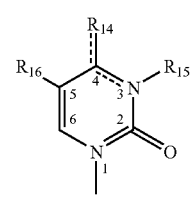

Formula V wherein:

$R_{10}$ and $R_{14}$ are hydroxy, oxo, amino, mercapto, alkylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or $R_{10}$ and $R_{14}$ are acylamino, provided that they incorporate an amino residue from the C-6 position of the purine or the C-4 position of the pyrimidine; or when $R_{10}$ in a purine or $R_{14}$ in a pyrimidine has as its first atom nitrogen, $R_{10}$ and $R_{11}$ or $R_{14}$ and $R_{15}$ are taken together to form a 5-membered fused imidazole ring (etheno compounds), optionally substituted on the etheno ring with alkyl, cycloalkyl, aralkyl, or aryl moieties, as described for $R_5$-$R_9$ above;

J is carbon or nitrogen, with the provision that when nitrogen, R12 is not present;

$R_{11}$ hydrogen, O (adenine 1-oxide derivatives) or is absent (adenine derivatives);

$R_{15}$ hydrogen, or acyl (e.g. acetyl, benzoyl, phenylacyl, with or without substituents); or $R_{12}$ hydrogen, alkyl, azido, alkylamino, arylamino or aralkylamino, alkoxy, aryloxy or aralkyloxy, alkylthio, arythio or aralkylthio, or $\omega$-A($C_{1-6}$alkyl)B- wherein A and B are independently amino, mercapto, hydroxy or carboxyl;

$R_{13}$ is hydrogen, chlorine, amino, monosubstituted amino, disubstituted amino, alkylthio, arylthio, or aralkylthio, where the substituent on sulfur contains up to a maximum of 20 carbon atoms, with or without unsaturation;

$R_{16}$ is hydrogen, methyl, alkyl, halo, alkyl, alkenyl, substituted alkenyl, alkynyl, or substituted alkynyl;

Compounds according to formulas IV and V where $R_{10}$ or $R_{14}$ is acylamino for the most part fall within the scope of formula VI:

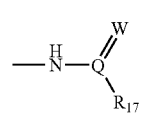

Formula VI wherein:

NH is the amino residue at the C-6 position in a purine or the amino residue at the C-4 position in a pyrimidine;

Q is a carbon atom;

W is oxygen or sulfur;

$R_{17}$ is amino or mono- or disubstituted amino such that the moiety according to formula VI is a urea or thiourea; or $R_{17}$ is alkoxy, aralkyloxy, aryloxy, substituted aralkyloxy, or substituted aryloxy, such that the moiety according to formula VI is a carbamate or thiocarbamate; or $R_{17}$ is alkyl, cycloalkyl, aralkyl, or aryl, with or without substituents or heteroatoms, such that the moiety according to formula VI is an amide.

The compounds of the present invention may be conveniently synthesized by those skilled in the art using well-known chemical procedures. Mononucloside mono-, di- and triphosphates may be obtained from commercial sources or may be synthesized from the nucleoside using a variety of phosphorylation reactions which may be found in the chemical literature. Symmetrical and unsymmetrical dinucleotide polyphosphates may be prepared by activation of a nucleoside mono-, di- or triphosphate with a coupling agent such as, but not limited to, dicyclohexylcarbodiimide or 1,1'-carbonyldiimidazole, followed by condensation with another nucleoside mono-, di-, or triphosphate, which may be the same or different as the activated moiety. Activation of nucleoside triphosphates with dicyclohexylcarbodiimide gives a cyclical trimetaphosphate as the activated species, which may be advantageously reacted with a variety of nucleophiles to install unique substituents on the terminal phosphate of a triphosphate.

The compounds of the present invention may be prepared by derivatization or substitution at the level of the nucleoside, followed by phosphorylation and condensation as previously described, or the reactions may be carried out directly on the preformed mono- or dinucleotides. In the general formulas Ia and Ib, the substituents at Y', Z', Y, and Z may be esters, carbamates, or carbonates, which are generally described by formula II. Esters may be readily prepared by reacting a hydroxyl group of the furanose in a nucleoside or nucleotide with an activated form of an appropriate organic acid, such as an acid halide or acid anhydride in the presence of an organic or inorganic base. Alternately, use of a suitable coupling reagent such as dicyclohexylcarbodiimide, 1,1'-carbonyldiimidazole and the like to activate the organic acid may be used to achieve the same result.

Carbamates or thiocarbamates may be most conveniently prepared by reaction of a hydroxyl group of the furanose in a nucleoside or nucleotide with any of a number of commercially available isocyanates or isothiocyanates, respectively, in an inert solvent. Alternately, when a desired isocyanate or isothiocyanate cannot be obtained from commercial sources, they may be prepared from the corresponding amine by the use of phosgene or thiophosgene, respectively, or their chemical equivalents. Carbonates or thiocarbonates may be synthesized by reacting the hydroxyl groups of a furanose in a nucleoside or nucleotide with an appropriate haloformate in the presence of an organic or inorganic base.

In the general formulas Ia and Ib, the substituents at Y'and Z', and Y and Z, when taken together, may be taken to mean acetals, ketals or orthoesters, as described in formula III. Acetals and ketals may be readily prepared by reaction of the neighboring 2' and 3' hydroxyl groups of the furanose in an appropriate nucleoside or nucleotide with an aldehyde or ketone, respectively, or their chemical equivalents, in the presence of an acid catalyst. Particularly advantageous is the use of an organic acid, which can effect the transformation without affecting the integrity of the rest of the molecule. Alternately, strong acids such as trichloroacetic, p-toluenesulfonic, methanesulfonic and the like may be employed in catalytic amounts, in conjunction with inert solvents. Most preferred is formic acid, which is ideally suited to serve as both solvent and catalyst for these reactions. The discovery of the utility of formic acid for this purpose is one particular aspect of this invention.

Cyclical orthoesters may be prepared by reaction of the neighboring 2' and 3' hydroxyl groups of a furanose with an acyclic orthoester, in the presence of an acid. When the nucleoside or nucleotide to be derivatized is a purine that contains a 6-amino functionality or is a pyrimidine that contains a 4-amino functionality, it may be converted to the respective urea or thiourea by treatment with isocyanates or isothiocyanates, respectively, as was previously described for carbamates or thiocarbamates of the 2' or 3' hydroxyls of the furanose. It was found that reactions of the amino group with isocyanates or isothiocyanates could be carried out in the presence of the hydroxyl groups of the furanose, by appropriate manipulation of the stoichiometry of the reaction.

All of the derivitization reactions described may be carried out on preformed dinucleotide polyphosphates, which results in multiple products dependent of reaction stoichiometry and on whether multiple reactive groups are present. When multiple products are obtained, these may be conveniently separated by the use of preparative reverse phase high performance liquid chromatography (HPLC). Particularly advantageous is the use of C18 or phenyl reverse phase columns, in conjunction with gradients that start with ammonium acetate buffer and end with methanol. The use of a buffer provides for nucleotide stability and improved peak shape of the eluting products and the use of methanol allows for effective desorption of these lipophilic compounds from the column. Particularly advantageous is the use of ammonium acetate buffer solutions in conjunction with methanol, as these solvents are miscible in all proportions and may be readily removed from the chromatographed products by evaporation, followed by lyophilization.

While separation of multiple products may be done by HPLC, another strategy is to use nucleosides or nucleotides which contain only a single reactive functionality, whether because only one is present, or by the use of protecting groups to block side reactions at other positions in the molecule. This may be done at the level of preformed dinucleotide polyphosphates, or alternately, may be carried out on nucleoside mono-, di-, or triphosphates, leading to novel products in their own right, or may be coupled to other nucleoside mono-, di-, or triphosphates by the methods which have already been described.

The novel compounds of the present invention are useful in therapy, in particular in the prevention of platelet aggregation. The compounds of the present invention are thus useful as anti-thrombotic agents, and are thus useful in the treatment or prevention of unstable angina, coronary angioplasty (PTCA) and myocardial infarction.

The compounds of the present invention are also useful in the treatment or prevention of primary arterial thrombotic complications of atherosclerosis such as thrombotic stroke, peripheral vascular disease, myocardial infarction without thrombolysis.

Still further indications where the compounds of the invention are useful are for the treatment or prevention of arterial thrombotic complications due to interventions in atherosclerotic disease such as angioplasty, endarterectomy, stent placement, coronary and other vascular graft surgery.

Still further indications where the compounds of the invention are useful are for the treatment or prevention of thrombotic complications of surgical or mechanical damage such as tissue salvage following surgical or accidental trauma, reconstructive surgery including skin flaps, and "reductive" surgery such as breast reduction.

The compounds of the present invention are also useful for the prevention of mechanically-induced platelet activation in vivo such as cardiopulmonary bypass (prevention of microthromboembolism), prevention of mechanically-induced platelet activation in vitro such as the use of the compounds in the preservation of blood products, e.g. platelet concentrates, prevention of shunt occlusion such as renal dialysis and plasmapheresis, thrombosis secondary to vascular damage/inflammation such as vasculities, arteritis, glomerulonephritis and organ graft rejection.

Still further indications where the compounds of the present invention are useful are indications with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

Still further indications where the compounds of the invention are useful are for the treatment or prevention of venous thrombosis such as deep vein thrombosis, veno-occlusive disease, hematological conditions such as thrombocythemia and polycythemia, and migraine.

In a particularly preferred embodiment of the present invention, the compounds are used in the treatment of unstable angina, coronary angioplasty and myocardial infarction.

In another particularly preferred embodiment of the present invention, the compounds are useful as adjunctive therapy in the prevention of coronary arterial thrombosis during the management of unstable angina, coronary angioplasty and acute myocardial infarction, i.e. perithrombolysis. Agents commonly used for adjunctive therapy in the treatment of thrombotic disorders may be used, for example heparin and/or aspirin, just to mention a few.

A method of treating a mammal to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

The compounds of this invention may be used in vitro to inhibit the aggregation of platelets in blood and blood products, e.g. for storage, or for ex vivo manipulations such as in diagnostic or research use. This invention also provides a method of inhibiting platelet aggregation and clot formation in a mammal, especially a human, which comprises the internal administration of a compound of formula (I) and a pharmaceutically acceptable carrier.

Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be useful in a method for the prevention of metastatic conditions, the prevention or treatment of fungal or bacterial infection, inducing immunostimulation, treatment of sickle cell disease, and the prevention or treatment of diseases in which bone resorption is a factor.

This invention further provides a method for inhibiting the reocclusion of an artery or vein following fibrinolytic therapy, which comprises internal administration of a compound of formula (I) and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule.

Extracorporeal circulation is routinely used for cardiovascular surgery in order to oxygenate blood. Platelets adhere to surfaces of the extracorporeal circuit. Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$ (wherein X is $C_{1-4}$). Pharmaceutically acceptable salts are salts that retain the desired biological activity of the parent compound and do not impart undesired toxicological effects.

EXAMPLE 1

2'(3')-O-((phenylaminocarbonyl)-uridine 5'-) triphosphate

Uridine 5"-triphosphate, ditributylammonium salt (100 mg, 0.176 mmol; prepared from the trisodium salt by treatment with Dowex 50W×4 $H^+$ in water, followed by mixing the protonated species with an excess of tributylamine, stripping and lyophilization) was dissolved in dry DMF (1 mL) and phenylisocyanate (19 uL, 0.176 mmol) added. The reaction mixture was heated at 45° C. for 15 minutes, at which point a further portion of phenylisocyanate (19 uL, 0.176 mmol) was added. The solution was heated at 45° C. overnight and the DMF was removed on a rotary evaporator. The residual oil was partitioned between water (2 mL) and ethyl acetate (2 mL) and the layers were separated. The aqueous layer was extracted twice more with ethyl acetate (2 mL each) and the water was removed on a rotary evaporator. The residue was dissolved in water (1.5 mL) and the product isolated by repeated injections onto a preparative HPLC column (Alltech Nucleotide/Nucleoside C18, 7 um, 10 X 250 mm, gradient from 0.1 M ammonium acetate to methanol over 30 minutes, 5 mL/min, monitor at 260 nm). The yield of the carbamate was 26 mg (22%, calculated for the tetraammonium salt). 1H NMR showed the product to be a mixture of 2' and 3' carbamates. The product so obtained can be used for the purposes of this invention per se or can be activated with a suitable coupling agent (e.g. a carbodiimide) and reacted with a variety of nucleotides to generate novel dinucleoside polyphosphates, or with non-nucleotide nucleophiles to give nucleotides bearing novel moieties on the terminal phosphate.

1H NMR (D2O, 300 MHz): δ 4.10–4.47 (m, 4H), 5.17 (m, 1H), 5.83 (dd, 1H), 5.96 (m, 1H), 7.04 (t, 1H), 7.25 (m, 4H), 7.79 (m, 1H). 31P NMR (D2O,121.47 MHz): δ -9.54 (m, 1P), -10.20 (m, 1P), -21.87 (m, 1P).

EXAMPLE 2

2'(3')-O-(phenylaminocarbonyl)-$P^1,P^4$-Di(uridine 5'-)tetraphosphate and $P^1,P^4$-Di-(2'(3')-O-(phenylaminocarbonyl)uridine 5'-)tetraphosphate $P^1,P^4$-Di(uridine 5'-) tetraphosphate, ditributylammonium salt (211 mg, 0.182 mmol; prepared from the tetrasodium salt by treatment with Dowex 50W×4 $H^+$ in water, followed by mixing the protonated species with an excess of tributylamine, stripping and lyophilization) was dissolved in dry DMF (2 mL) and phenylisocyanate (40 uL, 3.64 mmol) added in a single portion. The homogeneous reaction mixture was heated overnight at 45° C., whereupon TLC (silica gel, 50% isopropanol/50% ammonium hydroxide) indicated a substantial conversion to two products. The solvent was removed on a rotary evaporator and the residue was partitioned between water (7 mL) and ethyl acetate (10 mL). The layers were separated, and the aqueous was extracted twice more with ethyl acetate. (10 mL each). The water was removed from the aqueous extract and the residual oil lyophilized overnight. The solid obtained was reconstituted in water (3 mL) and the two products separated by repeated injections onto a semipreparative HPLC column (Alltech Nucleotide/Nucleoside C18, 7 um, 10 X 250 mm, gradient from 0.1 M ammonium acetate to methanol over 30 minutes, 5 mL/min, monitor at 260 nm). Stripping and lyophilization gave the mono-phenylcarbamate (48 mg, 27% yield), di-phenylcarbamate (16 mg, 8%yield) and a trace amount of the triphenylcarbamate, as the tetraammonium salts. All three products were mixtures of the corresponding 2'/3' regiosiomers.

Mono-phenylcarbamate: $^1$H NMR (D$_2$O, 300 MHz): δ 4.08-4.65 (m, 9H), 5.14 (d, 1H), 5.75-5.94 (m, 4H), 7.01 (t, 1H), 7.22 (m, 4H), 7.76 (m, 2H). $^{31}$P NMR (D$_2$O, 121.47 MHz): δ -10.17 (m, 2P), -21.81 (m, 2P).

Di-phenylcarbamate: $^1$H NMR (D$_2$O, 300 MHz): δ 4.13–4.43 (m, 8H), 5.12 (m, 2H), 5.84 (m, 4H), 7.01 (m, 2H), 7.21 (m, 8H), 7.75 (dd, 2H). $^{31}$P NMR (D$_2$O, 121.47 MHz): δ -10.19 (m, 2P), -21.65 (m, 2P).

Tri-phenylcarbamate: $^1$H NMR (D$_2$O, 300 MHz): δ 4.29 (m, 7H), 4.5.10 (m, 1H), 5.27 (m, 2H), 5.87 (m, 4H), 7.09 (m, 15H), 7.76 (d, 2H).). $^{31}$P NMR (D$_2$O, 121.47 MHz): δ -10.30 (m, 2P), -21.73 (m, 2P).

EXAMPLE 3

2',3'-(benzyl)methylenedioxy-$P^1,P^4$-Di(uridine 5'-)tetraphosphate and $P^1,P^4$-Di-(2',3'-((benzyl)methylenedioxy) uridine 5'-)tetraphosphate $P^1,P^4$-Di(uridine 5'-)tetraphosphate, tetrasodium salt (290 mg, 0.332 mmol) was dissolved in 98% formic acid and phenylacetaldehyde, dimethyl acetal (110 uL, 0.662 mmol) added. The reaction was stirred at ambient temperature for 3 days, at which point TLC (silica gel, 50% isopropanol/50% ammonium hydroxide) and HPLC (C18) showed good conversion to two less polar products. The formic acid was removed on a rotary evaporator, and the residue partitioned between 0.7 M ammonium bicarbonate (15 mL) and butyl acetate (15 mL). The layers were separated and the aqueous was washed with a further portion of butyl acetate (10 mL). The aqueous layer was stripped and the residue lyophilized overnight. The crude product was dissolved in water (5 mL) and the components separated by preparative HPLC (Waters Novapak C18, 6 um, 25 X 100 mm, gradient from 0.1 M ammonium acetate to methanol over 30 minutes, 30 mL/min, monitor at 260 nm). The yield of the monoacetal was 88 mg (28%) and of the diacetal 60 mg (17%), both as the tetraammonium salts.

Monoacetal: $^1$H NMR (D$_2$O, 300 MHz): δ 2.99 (d, 2H), 4.01-4.32 (m, 8H), 4.77 (m, 2H), 5.33 (m, 2H), 5.74 (d, 1H), 5.81 (m, 2H), 7.21 (m, 5H), 7.64 (d, 1H), 7.79 (d, 1H). $^{31}$P NMR (D$_2$O, 121.47 NHz): δ -10.18 (m, 1P), -10.78 (m, 1P), -22.00 (m, 2P).

Diacetal: $^1$H NMR (D$_2$O, 300 MHz): δ 2.98 (d, 4H), 3.99 (m, 4H), 4.27 (m, 2H), 5.27 (m, 2H), 5.36 (m, 2H), 5.73 (d, J=8.1 Hz, 2H), 7.21 (m, 10H), 7.61 (d, J=8.1 Hz, 2H). $^{31}$P NMR (D$_2$O, 121.47 MHz): δ -10.57 (m, 2P), -21.81 (m, 2P).

EXAMPLE 4

3'-O-(phenylaminocarbonyl)-2'-deoxy (uridine 5')-monophosphate

Deoxyuridine 5'-monophosphate, tetrabutylammonium salt (135 mg, 0.274 mmol; prepared from the disodium salt by treatment with Dowex 50W×4 $H^+$, following by stirring the resultant neutral species with excess tributylamine, stripping and lyophilization) was dissolved in dry DMF (1 mL). Phenylisocyanate (60 uL, 0.547 mmol) was added and the mixture heated overnight at 45° C., at which time TLC (silica gel, 50% isopropanol/50% ammonium hydroxide) and HPLC (C18) indicated a substantial conversion to a less polar product. The DMF was stripped on a rotary evaporator and the oily residue partitioned between water (10 mL) and ethyl acetate (10 mL). The layers were separated and the aqueous layer was rewashed with ethyl acetate (2 X 10 mL). The water was removed and the residue was dissolved in water (2 mL). The product was isolated by repeated injections onto semipreparative HPLC (Alltech Nucleotide/Nucleoside C18, 7 um, 10 X 250 mm, gradient from 0.1 M ammonium acetate to methanol over 30 minutes, 5 mL/min, monitor at 260 nm). The yield was 67 mg as the diammonium salt (53%).

$^1$H NMR (D$_2$O, 300 MHz): δ 2.21 (m, 2H), 3.84 (s, 2H), 4.13 (s, 1H), 5.08 (d, 1H), 5.63 (d, 1H), 6.06 (t, 1H), 6.89 (br. t, 1H), 7.10 (m, 4H), 7.72 (d, 1H). $^{31}$P NMR (D$_2$O, 121.47 MHz): δ -2.31 (s).

$P^1$-3'-O-(phenylaminocarbonyl)-2'-deoxyuridine 5'-)$P^4$-(uridine 5'-)tetraphosphate Uridine 5'-triphosphate, ditributylammonium salt (prepared from the trisodium salt by treatment with Dowex 50W×4 $H^+$, followed by stirring the resultant neutral species with excess tributylamine, stripping and lyophilization) is treated with 1.5 equivalents of dicyclohexylcarbodiimide in DMF for 2 hours at room temperature. The dicyclohexylurea is filtered off, and the resultant uridine 5'-cyclical triphosphate is treated with 3'-O-(phenylaminocarbonyl)-2'-deoxy (uridine 5')-monophosphate, which is in the monotributylammonium salt form. The reaction mixture is stirred for several days at 45° C., and the solvent is removed. The products are separated by preparative HPLC, as has been previously described.

EXAMPLE 5

2'(3')-2-methylamino)benzoyl-$P^1,P^4$-Di(uridine 5'-)tetraphosphate and $P^1,P^4$-Di-(2'(3')-(2-methylamino)benzoyl uridine 5'-)tetraphosphate $P^1,P^4$-Di(uridine 5'-) tetraphosphate, tetrasodium salt (800 mg, 0.93 mmol) was dissolved in water (5 mL) and the pH adjusted to 7.6 by the addition of solid sodium bicarbonate. N,N-dimethylformamide (DMF, 5 mL) was added, followed by N-methylisatoic anhydride (231 mg, 1.3 mmol) and the suspension was heated at 50° C. for 2.5 hrs. TLC (silica gel, 50% isopropanol, 50% ammonium hydroxide) indicated that the reaction was not done by this time, so a further portion of N-methylisatoic anhydride (100 mg, 0.56 mmol) was added and the reaction heated for another hour. The DMF was removed on a rotary evaporator and the residue was dissolved in a minimum of water and applied to a DEAE Sephadex A-25 column (3 X 60 cm). The column was eluted with a stepwise gradient from water to 1 M ammonium bicarbonate and the eluent monitored with a UV detector set at 254 nm. The two products that eluted were collected separately and the solvent was removed from each and the residue lyophilized overnight. $^1$H NMR indicated that the first product to elute was the monoacylated compound, while the latter was the diacylated derivative, and that both were mixtures with the acylation at either the 2' or 3' hydroxyls, but without two carbamates on the same sugar. The yield of the monoaminobenzoylated product was 150 mg (16%); the yield of the diaminobenzoylated compound was 91 mg (8.7%).

Monoaminobenzoylated derivative: $^1$H NMR (D$_2$O, 300 MHz): δ 2.70 (s, 3H), 4.09–4.55(m, 9H), 5.34 (m, 1H), 5.71 (m, 2H), 5.83 (dd, 1H), 6.01 (m, 1H), 6.57 (m, 1H), 6.65 (m, 1H), 7.25 (t, 1H), 7.72 (d, 2H), 7.81 (m, 2H). $^{31}$P NMR (D$_2$O, 121.47 MHz): δ -10.20 (m, 2P), −21.83 (m,2P).

Diaminobenzoylated derivative: $^1$H NMR (D$_2$O, 300 MHz): δ 2.69 (s, 6H), 4.15-4.51 (m, 8H), 5.27 (m, 2H), 5.86 (m, 4H), 6.60 (m, 4H), 7.30 (m, 2H), 7.79 (m, 4H). $^{31}$P NMR (D$_2$O, 121.47 MHz): δ -10.16 (m, 2P), -21.76 (m, 2P).

EXAMPLE 6

P$^1$-(4-N-(4-methoxyphenyl)aminocarbonylcytidine 5'-)-P$^4$-(uridine 5'-) tetraphosphate P$^1$-(cytidine 5'-)tetraphosphate, ditributylammonium salt (50 mg, 0.043 mmol: prepared from the tetraammonium salt by treatment with Dowex 50W×4 H$^+$ in water, followed by mixing the protonated species with an excess of tributylamine in methanol, stripping and lyophilization) was dissolved in dry DMF (1 mL) and tributylamine (10 uL, 0.43 mmol), and p-methoxyphenylisocyanate 8.4 uL, 0.648 mmol) were added in a single portion. The homogeneous reaction mixture was heated overnight at 35° C., whereupon TLC (silica gel, 50% isopropanol/50% ammonium hydroxide) and HPLC (C18) indicated a substantial conversion to a single product. The solvent was removed on a rotary evaporator and the residue dissolved in water (1 mL). The product was isolated by repeated injections onto a semi-preparative HPLC column (Alltech Nucleotide/Nucleoside C18, 7 um, 10 X 250 mm, gradient from 0.1 M ammonium acetate to methanol over 30 minutes, 5 mL/min, monitor at 260 nm). Stripping and lyophilization gave the p-methoxyphenylurea (b 24mg, 55% yield), as the tetraammonium salt.

The product so obtained can be derivatized on the 2' and/or 3' hydroxyl groups according to the foregoing methods (e.g. examples 2, 3,and 5).

$^1$H NMR (D$_2$O, 300 MHz): δ 3.59 (s, 3H), 4.01-4.20 (m, 10H), 5.68 (m, 3H), 6.19 (d, 1H), 6.71 (d, 2H), 7.18 (d, 2H), 7.67 (d, 1H), 8.06 (d, 1H). $^{31}$P NMR (D$_2$O, 121. 47 MHz): δ -10.13 (m, 2P), -21.76 (m, 2P).

EXAMPLE 7

P$^1$-((4-bromophenyl)ethenocytidine 5'-)-P$^4$-(uridine 5'-) tetraphosphate

P$^1$-(cytidine 5'-)-P$^4$-(uridine 5'-) tetraphosphate, tetrasodium salt (500 mg, 0.57 mmol) was dissolved in water (5 mL) and a solution of 2,4'- dibromoacetophenone (792 mg, 2.85 mmol) in DMF (15 mL) added. The mixture was heated overnight at 40° C., and a further portion of the dibromoketone (400 mg, 1.44 mmol) in DMF (5 mL) added. The rection was heated a further 5 hrs, and the solvents removed by evaporation. The residue was partitioned between water (20 mL) and ethyl acetate (25 mL) and the layers separated. The aqueous layer was washed with further ethyl acetate (2×15 mL) and the aqueous evaporated to dryness. The residue was dissolved in water (5 mL) and the product was isolated by repeated injections onto a semi-preparative HPLC column (see example 6 for conditions). The yield of the pure etheno compound was 80 mg (13.5%)

$^1$H NMR (D$_2$O, 300 MHz): δ 4.06 (m, 8H), 4.36 (m, 2H), 5.64 (dd, 2H), 6.07 (d, 1H), 6.74 (d, 1H), 7.45 (d, 2H), 7.54 (d, 2H), 7.59 (d, 1H), 7.63 (d, 1H), 7.93 (s, 1H). $^{31}$P NMR (D$_2$O, 121.47 MHz): δ -10.09 (m, 2P), -21.59 (m, 2P).

EXAMPLE 8

P$^1$-((4-bromophenyl)etheno-2'-deoxycytidine 5'-)-P$^4$-(uridine 5'-) tetraphosphate Example 8 product was prepared from 100 mg P$^1$-(2'-deoxycytidine 5'-)-P$^4$-(uridine 5'-) tetraphosphate, tetrasodium salt and 2,4'-dibromoacetophenone, according to the general method of example 7. Yield=35 mg (30%).

$^1$H NMR (D$_2$O, 300 MHz): δ 2.31 (m, 2H), 4.03 (m, 8H), 5.60 (dd, 2H), 6.41 (t, 1H), 6.73 (d, 1H), 7.53 (m, 5H), 7.65 (d, 1H), 7.93 (s, 1H). $^{31}$P NMR (D$_2$O, 121.47 MHz): δ -10.11 (m, 2P), -21.58 (m, 2P).

EXAMPLE 9

P$^1$, P$^4$-Di((4-bromophenyl)ethenocytidine 5'-)-tetraphosphate

Example 9 product was prepared from 50 mg P$^1$,P4-Di (cytidine 5'-) tetraphosphate, tetrasodium salt and 2,4'-dibromoacetophenone, according to the general method of example 7. Yield=20 mg (29%).

$^1$H NMR (D$_2$O, 300 MHz): δ 4.24 (m, 10H), 5.98 (d, 2H), 6.39 (d, 2H), 7.14 (m, 8H), 7.45 (m, 4H).). $^{31}$P NMR (D$_2$O, 121.47 MHz): β -10.13 (m, 2P), -21.68 (m, 2P).

EXAMPLE 10

P$^1$-((4-phenylphenyl)ethenocytidine 5'-)-P$^4$-(cytidine 5'-) tetraphosphate

Example 10 was product prepared from 50 mg P$^1$,P4-Di (cytidine 5'-) tetraphosphate, tetrasodium salt and 2-bromo-4'-phenylacetophenone, according to the general method of example 7. Yield=15 mg (13%). $^1$H NMR (D$_2$O, 300 MHz): β 4.10 (m, 10H), 5.48 (d, 1H), 5.87 (m, 2H), 6.68 (d, 1H), 7.20 (m, 3H), 7.36 (m, 6H), 7.68 (m, 3H). $^{31}$P NMR (D$_2$O, 121.47 MHz): δ -10.08 (m, 2P), -21.78 (m, 2P).

The products of examples 7–10 can be further derivatized according to the methods of examples 2, 3, and 5, to give bifunctional molecules that fall within the scope of the invention.

Those skilled in the art will recognize various synthetic methodologies which may be employed to prepare non-toxic pharmaceutically acceptable salts and acylated prodrugs of the compounds.

The active compounds may be administered systemically to target sites in a subject in need such that the extracellular concentration of a P2Y$_\tau$ antagonist is elevated to block the binding of ADP to $P2Y_\tau$ receptors, thus inhibit the platelet aggregation. The term systemic as used herein includes subcutaneous injection, intravenous, intramuscular, intrasternal injection, intravitreal injection, infusion, inhalation, transdermal administration, oral administration, rectal administration and intra-operative instillation.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile indictable preparation may be a sterile indictable solution or suspension in a non-toxic acceptable diluent or solvent. Among the acceptable vehicles and solvents that may be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use may also be presented as chewable gums by embedding the active ingredient in gums so that the active ingredient is slowly released upon chewing.

Additional means of systemic administration of the active compound to the target platelets of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds may also be systemically administered to the platelet aggregation sites through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs, and subsequently contact the target platelets in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another method of systemically administering the active compounds to the platelet aggregation sites of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

Intravitreal delivery may include single or multiple intravitreal injections, or via an implantable intravitreal device that releases $P2Y_\tau$ antagonists in a sustained capacity. Intravitreal delivery may also include delivery during surgical manipulations as either an adjunct to the intraocular irrigation solution or applied directly to the vitreous during the surgical procedure.

For systemic administration, plasma concentrations of active compounds delivered may vary according to compounds; but are generally $1 \times 10^{-10} - 1 \times 10^{-5}$ moles/liter, and preferably $1 \times 10^{-8} - 1 \times 10^{-6}$ moles/liter.

The pharmaceutical utility of P2Y agonist compounds of this invention are indicated by the inositol phosphate assay for P2Y activity. This widely used assay, as described in E. Lazarowski, et al., *Brit. J. Pharm.* 116, 1619–27 (1995), relies on the measurement of inositol phosphate formation as a measurement of activity of compounds activating receptors linked via G-proteins to phospholipase C.

The invention is illustrated further by the following examples which are not to be construed as limiting the invention in scope or spirit to the specific procedures described in them.

EXAMPLE 11

Inhibition of ADP-Induced Platelet Aggregation

*Isolation of Platelets:* Human blood was obtained from informed healthy volunteers. Blood was collected into onesixth volume of ACD (2.5 g of sodium citrate, 1.5 g citric acid, and 2.5 g glucose in 100 ml dH$_2$O). Blood was centrifuged at 800×g for 15 min at room temperature and the platelet-rich plasma removed and incubated for 60 min at 37° C. in the presence of 1 mM acetylsalicylic acid followed by centrifugation at 1000×g for 10 min at room temperature. The platelet pellet was resuspended at a density of 2×10$^8$ cells/ml with HEPES-buffered Tyrode's solution (137 mM NaCl, 2.7 mM KCl, 1 mM MgCl$_2$, 3 mM NaH$_2$PO$_4$, 5 mM glucose, 10 mM HEPES pH 7.4, 0.2% bovine serum albumin, and 0.05 U/ml apyrase).

*Aggregation Studies*: ADP-induced platelet aggregation was determined by measuring the transmission of light through a 0.5 ml suspension of stirred (900 rpm) aspirin-treated washed platelets in a lumi-aggregometer at 37° C. (Chrono-Log Corp. Havertown, Pa.). The baseline of the instrument was set using 0.5 ml of Hepes-buffered Tyrode's solution. Prior to aggregation measurements, the platelet suspension was supplemented with 2 mM CaCl$_2$ and 1 mg/ml fibrinogen. Platelet aggregation was initiated by the addition of indicated concentrations of ADP or other agonists, and the light transmission continuously recorded for at least 8 min. When inhibitors of platelet aggregation were tested, platelets were incubated for 3–6 min in the presence of indicated concentrations of inhibitor before addition of ADP or other agonists, and the response recorded for at least 8 min. The potency of agonists and inhibitors of platelet aggregation were estimated from both, the rate of aggregation and the maximal extent of aggregation obtained for each determination by fitting the data to a four parameter logistic equation (Graph-Pad Corp).

EXAMPLE 12

Effects on Platelet Aggregation In Vivo

To evaluate the ability of these compounds to inhibit platelet aggregation in vivo, an experimental protocol similar to the method of R. G. Humphries et al. (Br. J. Pharmacol. 115:1110–1116, 1995) will be performed.

*Surgical Preparation and Instrumentation:* Male Sprague-Dawley rats are anesthetized. Body temperature is maintained at 37±0.5° C. with a heating lamp. Animals breathe spontaneously and a tracheotomy is performed to ensure a patent airway. A cannula containing heparinized saline is introduced into the left femoral artery and connected to a transducer to record blood pressure and heart rate. Cannulae containing non-heparinized saline are introduced into the left common carotid artery and left jugular vein for withdrawal of arterial blood samples and i.v. administration of compounds.

*Experimental Protocol:* Either compound or vehicle is administered to each animal as an infusion. Blood samples are taken immediately prior to the first infusion, at the end of each infusion and 20 min after cessation of the final infusion for measurement of platelet aggregation ex vivo. Immediately after sampling, ADP-induced platelet aggregation is measured in duplicate in 0.5 ml blood samples diluted 1:1 with saline and incubated at 37° C. for 4 min. For the final minute of this period, cuvettes are transferred to a lumi-aggregometer and the sample stirred at 900 rpm. ADP (3M) is added in a volume of 20 1 and the aggregation response is recorded.

EXAMPLE 13

Inhibition of Thrombus Formation in Anesthetized Rats

To evaluate the effect of these compounds on thrombus formation in vivo, the following experimental protocol will be performed.

Rats (CD-1; male; approximately 350 grams; Charles River, Raleigh, N.C.), are anesthetized with sodium pentobarbital (70 mg/kg i.p.). The abdomens are shaved and a 22 gauge intravenous catheter is inserted into a lateral tail vein. A midline incision is made and the intestines are wrapped in saline-soaked gauze and positioned so the abdominal aorta is accessible. The inferior vena cava and abdominal aorta are carefully isolated and a section (approx. 1 cm) of the abdominal aorta (distal to the renal arteries proximal to the bifurcation) is dissected. All branches from the aorta in this section are ligated with 4–0 silk suture. A 2.5 mm diameter flow probe connected to a Transonic flow meter is placed on the artery and a baseline (pre-stenosis) flow is recorded. Two clips are placed around the artery decreasing the vessel diameter by approximately 80%. A second baseline flow measurement is taken (post-stenosis) and the hyperemic response is tested. Animals are then treated with either compound or saline i.v., via tail vein catheter. Thrombosis is induced five minutes after treatment by repeated external compressions of the vessel with hemostatic forceps. Two minutes post-injury, the vessel compressions are repeated and a 10 minute period of flow monitoring is started. Animals are monitored continuously for a minimum of the first ten minutes post-injury. After twenty minutes (post-injury), a flow measurement is repeated and the animals are euthanized. The section of the aorta that includes the injured section is harvested and placed in 10% formalin for possible histologic evaluation.

EXAMPLE 14

Inhibition of Thrombus Formation in Anesthetized Dogs

To evaluate the effect of these compounds on dynamic thrombus formation in vivo, the following experimental protocol similar to the method of J. L. Romson et al. (Thromb. Res. 17:841–853, 1980) will be performed.

*Surgical Preparation and Instrumention:* Briefly, purpose-bred dogs are anesthetized, intubated and ventilated with room air. The heart is exposed by a left thoracotomy in the fifth intercostal space and suspended in a pericardial cradle. A 2–3 cm segment of the left circumflex coronary artery (LCCA) is isolated by blunt dissection. The artery is instrumented from proximal to distal with a flow probe, a stimulation electrode, and a Goldblatt clamp. The flow probe monitors the mean and phasic LCCA blood flow velocities. The stimulation electrode and its placement in the LCCA and the methodology to induce an occlusive coronary thrombus have been described previously (J. K. Mickelson et al., Circulation 81:617–627, 1990; R. J. Shebuski et al., Circulation 82:169–177, 1990; J. F. Tschopp et al., Coron. Artery Dis. 4:809–817, 1993).

*Experimental Protocol:* Dogs are randomized to one of four treatment protocols (n=6 per treatment group) in which the control group receives saline i.v. and the three drug-treated groups are administered compound i.v. Upon stabilization from the surgical interventions, dogs receive either saline or compound. After approximately 30 minutes, an anodal current is applied to the LCCA for 180 min. The number and frequency of cyclic flow variations (CFV) that precede formation of an occlusive thrombus are recorded. These cyclic phenomena are caused by platelet thrombi that form in the narrowed lumen as a result of platelet aggregation (J. D. Folts et al., Circulation 54:365–370, 1976; Bush et al., Circulation 69:1161–1170, 1984). Zero flow in the LCCA for a minimum of 30 minutes indicates a lack of antithrombotic efficacy (L.G. Frederick et al., Circulation 93:129–134, 1996).

Although the foregoing invention has been described in some detail by way of illustration and example for purposes of clarity of understanding, it will be obvious that certain changes and modifications may be practiced within the scope of the appended claims.

All publications, patents, and patent applications are herein incorporated by reference in their entirety to the same extent as if individual publication, patent, or patent application was specifically and individually indicated to be incorporated by reference in its entirety.

What is claimed:

1. A pharmaceutical formulation comprising a compound of general formula I, or salts thereof:

Formula I

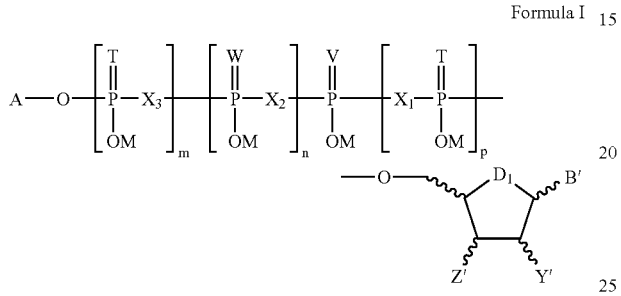

wherein:
- $X_1$, $X_2$, and $X_3$ are independently selected from the group consisting of oxygen, methylene, monochloromethylene, dichloromethylene, monofluoromethylene, difluoromethylene, and imido;
- T, W, and V are independently oxygen or sulfur;
- m=0, 1 or 2;
- n=0, 1, or 2;
- p=0, 1, or 2;
- M=H or a pharmaceutically-acceptable inorganic or organic counterion;
- $D_1$=O or C;
- B' is a purine or a pyrimidine residue according to general formulas IV and V which is linked to the 1' position of the furanose or carbocycle via the 9- or 1-position, respectively;
- A is M or alkyl; or
- A is a nucleoside residue which is defined as:

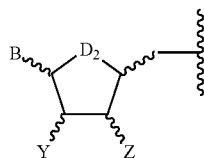

and which is linked to the phosphate chain via the 5' position of the furanose or carbocycle;

wherein:
- $D_2$=O or C;
- B is a purine or a pyrimidine residue according to general formulas IV and V which is linked to the sugar or carbocycle via the 9- or 1-position, respectively;
- wherein when $D_1$ and $D_2$ are oxygen, the furanose is in the β-configuration;
- Y'=H, OH, or $OR_1$, where $OR_1$ falls under the definition of general Formula II or III;
- Z'=OH or $OR_2$, where $OR_2$ falls under the definition of general Formula II or III;
- Z=OH or $OR_3$, where $OR_3$ falls under the definition of general formula II or III;
- Y=H, OH, or $OR_4$, where $OR_4$ falls under the definition of general Formula II or III;
- provided that at least one of Y', Z', Z, and Y is $OR_1$, $OR_2$, $OR_3$, or $OR_4$, respectively;
- wherein compounds of general Formula I are molecules whose structures fall within the definitions of Formula Ia and Formula Ib:

Formula Ia

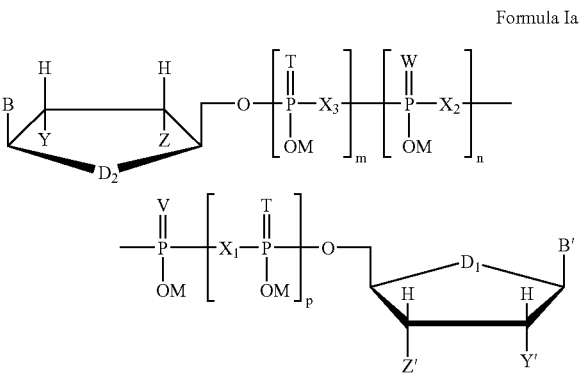

$X_1$, $X_2$, and $X_3$=O;
T, V, and W=O;
M=H, $NH_4^+$, $Na^+$ or other pharmaceutically-acceptable inorganic or organic counterion;
Y'=H, OH, or $OR_1$, where $OR_1$ falls under the definition of general formula II;
Z'=OH or $OR_2$, where $OR_2$ falls under the definition of general formula II;
Z=OH or $OR_3$, where $OR_3$ falls under the definition of general formula II;
Y=H, OH, or $OR_4$, where $OR_4$ falls under the definition of general formula II;
provided that at least one of Y', Z', Z, and Y is $OR_1$, $OR_2$, $OR_3$, or $OR_4$, respectively;
$D_1$=O;
$D_2$=O or C;
B and B' are purine or pyrimidine residues according to general formulas IV and V;
m and p=0, 1 or 2;
n=0 or 1;
such that the sum of m+n+p is from 0 to 5; or
$X_1$, $X_2$, and $X_3$=O;
T, V, and W=O;
M=H, $NH_4^+$, $Na^+$ or other pharmaceutically-acceptable inorganic or organic counterion;
Y'=H, OH, or $OR_1$, where $OR_1$ falls under the definition of general formula III;
Z'=OH or $OR_2$, where $OR_2$ falls under the definition of general formula III;
Z=OH or $OR_3$, where $OR_3$ falls under the definition of general formula III;
Y=H, OH, or $OR_4$, where $OR_4$ falls under the definition of general formula III;
provided that at least one of Y', Z', Z, and Y is $OR_1$, $OR_2$, $OR_3$, or $OR_4$, respectively;
$D_1$=O;
$D_2$=O or C;

B and B' are purine or pyrimidine residues according to general formulas IV and V;

m and p=0, 1 or 2;

n=0 or 1;

such that the sum of m+n+p is from 0 to 5; or $X_1$ and $X_3$=O;

$X_2$ is selected from the group consisting of methylene, monochloromethylene, dichloromethylene, monofluoromethylene, difluoromethylene, and imido;

T, V, and W=O;

M=H, $NH_4^+$, $Na^+$ or other pharmaceutically-acceptable inorganic or organic counterion;

Y'=H, OH, or $OR_1$, where $OR_1$ falls under the definition of general formula II;

Z'=OH or $OR_2$, where $OR_2$ falls under the definition of general formula II;

Z=OH or $OR_3$, where $OR_3$ falls under the definition of general formula II;

Y=H, OH, or $OR_4$, where $OR_4$ falls under the definition of general formula II;

provided that at least one of Y', Z', Z, and Y is $OR_1$, $OR_2$, $OR_3$, or $OR_4$, respectively;

$D_1$=O;

$D_2$=O or C;

B and B' are purine or pyrimidine residues according to general formulas IV and V;

m and p=0, 1 or 2;

n=1;

such that the sum of m+n+p is from 0 to 5; or $X_1$ and $X_3$=O;

$X_2$ is selected from the group consisting of methylene, monochloromethylene, dichloromethylene, monofluoromethylene, difluoromethylene, and imido;

T, V, and W=O;

M=H, $NH_4^+$, $Na^+$ or other pharmaceutically-acceptable inorganic or organic counterion;

Y'=H, OH, or $OR_1$, where $OR_1$ falls under the definition of general formula III;

Z'=OH or $OR_2$, where $OR_2$ falls under the definition of general formula III;

Z=OH or $OR_3$, where $OR_3$ falls under the definition of general formula III;

Y=H, OH, or $OR_4$, where $OR_4$ falls under the definition of general formula III;

provided that at least one of Y', Z', Z, and Y is $OR_1$, $OR_2$, $OR_3$, or $OR_4$, respectively;

$D_1$=O;

$D_2$ is O or C;

B and B' are purine or pyrimidine residues according to general formulas IV and V;

m and p=0, 1 or 2;

n=1;

such that the sum of m+n+p is from 0 to 5; or $X_1$ and $X_3$=O;

$X_2$ is selected from the group consisting of methylene, monochloromethylene, dichloromethylene, monofluoromethylene, difluoromethylene, and imido;

T=S;

V and W=O;

M=H, $NH_4^+$, $Na^+$ or other pharmaceutically-acceptable inorganic or organic counterion;

Y'=H, OH, or $OR_1$, where $OR_1$ falls under the definition of general formula II;

Z'=OH or $OR_2$, where $OR_2$ falls under the definition of general formula II;

Z=OH or $OR_3$, where $OR_3$ falls under the definition of general formula II;

Y=H, OH, or $OR_4$, where $OR_4$ falls under the definition of general formula II;

provided that at least one of Y', Z', Z, and Y is $OR_1$, $OR_2$, $OR_3$, or $OR_4$, respectively;

$D_1$=O;

$D_2$=O or C;

B and B' are purine or pyrimidine residues according to general formulas IV and V;

m, n and p=1; or $X_1$ and $X_3$=O;

$X_2$ is selected from the group consisting of methylene, monochloromethylene, dichloromethylene, monofluoromethylene, difluoromethylene, and imido;

T=S;

V and W=O;

M is selected from the group consisting of H, $NH_4^+$, $Na^+$ and other pharmaceutically-acceptable inorganic or organic counterion;

Y'=H, OH, or $OR_1$, where $OR_1$ falls under the definition of general formula III;

Z'=OH or $OR_2$, where $OR_2$ falls under the definition of general formula III;

Z=OH or $OR_3$, where $OR_3$ falls under the definition of general formula III;

Y=H, OH, or $OR_4$, where $OR_4$ falls under the definition of general formula III;

provided that at least one of Y', Z', Z, and Y is OR1, OR2, OR3, or OR4, respectively;

$D_1$=O;

$D_2$=O or C;

B and B' are purine or pyrimidine residues according to general formulas IV and V;

m, n, and p=1;

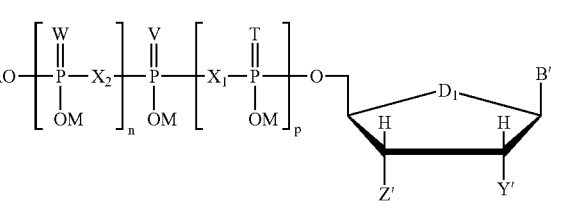

Formula Ib wherein:

A is M or alkyl;

$X_1$ and $X_2$=O;

T, V, and W=O;

M=H, $NH_4^+$, Na or other pharmaceutically-acceptable inorganic or organic counterion;

Y'=H, OH, or $OR_1$, where $OR_1$ falls under the definition of general formula II;

Z'=H, OH or $OR_2$, where $OR_2$ falls under the definition of general formula II;

with the provision that at least one of Y' and Z' is $OR_1$ or $OR_2$;

$D_1$=O or C;

B' is purine or pyrimidine residue according to general formulas IV and V;

n and p are 0, 1, or 2 such that the sum of n+p is from 1 to 3; or

A is M or alkyl;

$X_1$ and $X_2$=O;

T, V, and W=O;

M is selected from the group consisting of H, $NH_4^+$, $Na^+$ and other pharmaceutically-acceptable inorganic or organic counterion;

Y'=$OR_1$, where $OR_1$ falls under the definition of general formula III;

Z'=$OR_2$, where $OR_2$ falls under the definition of general formula III;

$D_1$=O or C;

B' is purine or pyrimidine residue according to general formulas IV and V;

n and p are 0, 1, or 2 such that the sum of n+p is from 1 to 3; or

A is M or alkyl;

$X_1$ and $X_2$=O;

T and V=O;

W=S;

M=H, $NH_4^+$, $Na^+$ or other pharmaceutically-acceptable inorganic or organic counterion;

Y'=H, OH, or $OR_1$, where $OR_1$ falls under the definition of general formula II;

Z'=H, OH or $OR_2$, where $OR_2$ falls under the definition of general formula II;

with the provision that at least one of Y' and Z' is $OR_1$ or $OR_2$;

$D_1$=O or C;

B' is purine or pyrimidine residue according to general formulas IV and V;

p is 0, 1, or 2 such that the sum of n+p is from 1 to 3; n=1; or

A is M or alkyl;

$X_1$ and $X_2$=O;

T and V=O;

W=S;

M is selected from the group consisting of H, $NH_4^+$, $Na^+$ and other pharmaceutically-acceptable inorganic or organic counterion;

Y'=$OR_1$, where $OR_1$ falls under the definition of general formula III;

Z'=$OR_2$, where $OR_2$ falls under the definition of general formula III;

$D_1$=O or C;

B' is purine or pyrimidine residue according to general formulas IV and V;

p is 0, 1, or 2 such that the sum of n+p is from 1 to 3; n=1; or

A is M or alkyl;

$X_1$=O;

$X_2$ is selected from the group consisting of methylene, monochloromethylene, dichloromethylene, monofluoromethylene, difluoromethylene, and imido;

T, V, and W=O;

M is selected from the group consisting of H, $NH_4^+$, $Na^+$ and other pharmaceutically-acceptable inorganic or organic counterion;

Y'=H, OH, or $OR_1$, where $OR_1$ falls under the definition of general formula II;

Z'=H, OH or $OR_2$, where $OR_2$ falls under the definition of general formula II;

with the provision that at least one of Y' and Z' is $OR_1$ or $OR_2$;

$D_1$=O or C;

B' is purine or pyrimidine residue according to general formulas IV and V;

p is 0, 1, or 2 such that the sum of n+p is from 1 to 3; n=1; or

A is M or alkyl;

$X_1$=O;

$X_2$ is selected from the group consisting of methylene, monochloromethylene, dichloromethylene, monofluoromethylene, difluoromethylene, and imido;

T, V, and W=O;

M is selected from the group consisting of H, $NH_4^+$, $Na^+$ and other pharmaceutically-acceptable inorganic or organic counterion;

Y'=H, OH, or $OR_1$, where $OR_1$ falls under the definition of general formula III;

Z'=H, OH or $OR_2$, where $OR_2$ falls under the definition of general formula III;

$D_1$=O or C;

B' is purine or pyrimidine residue according to general formulas IV and V;

p is 0, 1, or 2 such that the sum of n+p is from 1 to 3; n=1;

wherein, for compounds according to Formula Ia or Ib, where Y'=$OR_1$, Z'=$OR_2$, Z=$OR_3$ and/or Y=$OR_4$, at least one of the four is a residue which is linked directly to the corresponding 2' or 3' hydroxyl oxygen of the furanose or carbocycle via a carbon atom; wherein said residue falls within the scope of formula II or formula III:

$$\xi\!-\!O\!-\!Q\!\begin{array}{c}R_5\\\diagup\\\diagdown\\R_7\end{array}\!\!R_6 \qquad \text{Formula II}$$

wherein:

O is the corresponding 2' or 3' oxygen of the furanose or carbocycle;

$R_5$, $R_6$, and $R_7$ are selected from the group consisting of H, an alkyl, cycloalkyl, aralkyl, aryl, substituted aralkyl, and substituted aryl, such that the moiety defined according to formula II is an ether; or $R_5$ and $R_6$ are taken together to be oxygen or sulfur doubly bonded to Q, and $R_7$ is selected from the group consisting of alkyl, cycloalkyl, aralkyl, and substituted aralkyl, such that the moiety defined according to formula II is an ester or thioester; or $R_5$ and $R_6$ are taken together to be oxygen or sulfur doubly bonded to Q, and $R_7$ is amino or mono- or disubstituted amino, where the substituents are selected from the group consisting of alkyl, cycloalkyl, aralkyl, aryl, substituted aralkyl, and substituted aryl, such that the moiety according to formula II is a carbamate or thiocarbamate; or $R_5$ and $R_6$ are taken together to be oxygen or sulfur doubly bonded to Q, and $R_7$ is selected from the group consisting of alkoxy, cycloalkoxy, aralkyloxy, aryloxy, substituted aralkyloxy, and substituted aryloxy, such that the moiety according to formula II is a carbonate or thiocarbonate; or $R_5$ and $R_6$ are taken together to be oxygen or sulfur doubly bonded to Q and both the 2' and 3' oxygens of the furanose are directly bound to Q to form a cyclical carbonate or thiocarbonate, $R_7$ is not present;

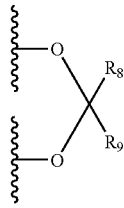

Formula III wherein:
O is the 2' and 3' oxygens of the furanose or carbocycle; and the 2' and 3' oxygens of the furanose or carbocycle are linked by a common carbon atom to form a cyclical acetal, cyclical ketal, or cyclical orthoester; and for cyclical acetals and ketals, $R_8$ and $R_9$ are independently selected from the group consisting of hydrogen, alkyl, cycloalkyl, aralkyl, aryl, substituted aralkyl, and substituted aryl; or are joined together to form a homocyclic or heterocyclic ring composed of 3 to 8 atoms, or for cyclical orthoesters, $R_8$ is selected from the group consisting of hydrogen, alkyl, cycloalkyl, aralkyl, aryl, substituted aralkyl, and substituted aryl, and $R_9$ is selected from the group consisting of alkyloxy, cycloalkyloxy, aralkyloxy, aryloxy, substituted aralkyloxy, and substituted aryloxy;

B and B' are independently a purine residue, as in formula IV, linked through the 9-position, or a pyrimidine residue, as in formula V, linked through the 1-position;

wherein, provided when $D_1$ and $D_2$ are oxygen, the ribosyl moieties are in the D-configuration;

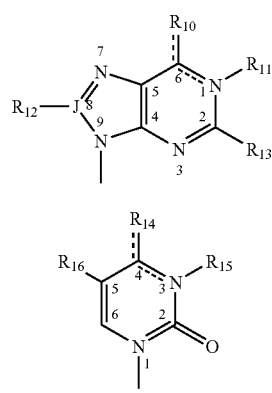

Formula IV

Formula V wherein:
$R_{10}$ and $R_{14}$ are selected from the group consisting of hydroxy, oxo, amino mercapto, alkylthio, alkyloxy, aryloxy, alkylamino, cycloalkylamino, aralkylamino, arylamino, diaralkylamino, diarylamino, and dialkylamino, where the alkyl groups are optionally linked to form a heterocycle; or $R_{10}$ and $R_{14}$ are acylamino according to Formula VI, provided that they incorporate an amino residue from the C-6 position of the purine or the C-4 position of the pyrimidine; or when $R_{10}$ in a purine or $R_{14}$ in a pyrimidine has as its first atom nitrogen, $R_{10}$ and $R_{11}$ or $R_{14}$ and $R_{15}$ are taken together to form a 5-membered fused imidazole ring, optionally substituted on the etheno ring with $R_5$–$R_9$ selected from the group consisting of alkyl, cycloalkyl, aralkyl, or aryl moieties, as described above;

J is carbon or nitrogen, with the provision that when nitrogen, $R_{12}$ is not present;

$R_{11}$ is hydrogen, O or is absent;

$R_{12}$ is selected from the group consisting of hydrogen, alkyl, azido, alkylamino, arylamino, aralkylamino, alkoxy, aryloxy, aralkyloxy, alkylthio, arythio, aralkylthio, and ω-$A(C_{1-6}alkyl)B$- wherein A and B are selected from the group consisting of independently amino, mercapto, hydroxy and carboxyl;

$R_{13}$ is selected from the group consisting of hydrogen, chlorine, amino, monosubstituted amino, disubstituted amino, alkylthio, arylthio, and aralkylthio, where the substituent on sulfur contains up to a maximum of 20 carbon atoms, with or without unsaturation;

$R_{15}$ is selected from the group consisting of hydrogen, and acyl, such as acetyl, benzoyl, phenylacyl, with or without substituents;

$R_{16}$ is selected from the group consisting of hydrogen, methyl, alkyl, halo, alkyl, alkenyl, substituted alkenyl, alkynyl, and substituted alkynyl;

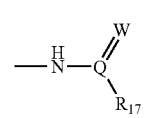

Formula VI wherein:
NH is the amino residue at the C-6 position in a purine or the amino residue at the C-4 position in a pyrimidine;

Q is a carbon atom;

W is oxygen or sulfur;

$R_{17}$ is amino or mono- or disubstituted amino such that the moiety according to formula VI is a urea or thiourea; or $R_{17}$ is selected from the group consisting of alkoxy, aralkyloxy, aryloxy, substituted aralkyloxy, and substituted aryloxy, such that the moiety according to formula VI is a carbamate or thiocarbamate; or $R_{17}$ is selected from the group consisting of alkyl, cycloalkyl, aralkyl, and aryl, with or without substituents or heteroatoms, such that the moiety according to formula VI is an amide.

2. The compound according to claim 1, wherein said compound is fluorescently labeled and used as a biochemical probe for the $P2_T$ receptor.

3. A method of treating diseases or conditions associated with platelet aggregation comprising:
administering to a patient a pharmaceutical formulation according to claim 1, wherein said compound is effective to bind the $P2_T$ receptors on platelets and inhibit ADP-induced platelet aggregation.

4. The method according to claim 3, wherein said pharmaceutical formulation is administered to reduce the incidence of dose-related adverse side effects of other therapeutic agents used to prevent, manage or treat platelet aggregation disorders.

5. The method according to claim 3, wherein said administering is systemic administration of said compound.

6. The method according to claim 5, wherein said systemic administration is administration of an injectable form of said compound, such that a therapeutically effective amount of said compound contacts the target platelets of said patient via systemic absorption and circulation.

7. The method according to claim 5, wherein said systemic administration is accomplished by administering an oral form of said compound, such that a therapeutically effective amount of said compound contacts the target platelets of said patient via systemic absorption and circulation.

8. The method according to claim 5, wherein said systemic administration is administration of said compound in a form of a transdermal patch or a transdermal pad, such that a therapeutically effective amount of said compound contacts the target platelets of said patient via systemic absorption and circulation.

9. The method according to claim 5, wherein said systemic administration is administration of a liquid/liquid suspension of said compound via nose drops or nasal spray, or administration of a nebulized liquid to oral or nasopharyngeal airways of said subject, such that a therapeutically effective amount of said compound inhibits platelet aggregation.

10. The method according to claim 5, wherein said systemic administration comprises infusion of said compound to target platelets via a device selected from a group consisting of a pump catheter system and a continuous or selective release device.

11. The method according to claim 5, wherein said systemic administration is administration of a suppository form of said compound, such that a therapeutically effective amount of said compound contacts the target platelets of said patient via systemic absorption and circulation.

12. The method according to claim 5, wherein said systemic administration is vaginal administration in dosage unit formulations containing conventional non-toxic pharmaceutically acceptable carriers, adjuvants and vehicles.

13. The method according to claim 5, wherein said compound is administered to a patient by an intravitreal delivery.

14. The method according to claim 5, wherein said systemic administration is administration of an intraoperative instillation of a gel, cream, powder, foam, crystals, liposomes, spray or liquid suspension form of said compound, such that a therapeutically effective amount of said compound contracts the target platelets of said patient via systemic absorption and circulation.

15. The method according to claim 3, wherein said diseases or conditions associated with platelet aggregation are disorders or procedures characterized by thrombosis, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, venous thrombosis, coronary arterial thrombosis, pathological effects of atherosclerosis and arteriosclerosis, platelet aggregation and clot formation in blood and blood products during storage, chronic or acute states of hyper-aggregability, reocclusion of an artery or vein following fibrinolytic therapy, platelet adhesion associated with extracorporeal circulation, thrombotic complications associated with thrombolytic therapy, thrombotic complications associated with coronary and other angioplasty, or thrombotic complications associated with coronary artery bypass procedures.

16. The method according to claim 15, wherein said disorders or procedures characterized with thrombosis are unstable angina, coronary angioplasty, or myocardial infarction.

17. The method according to claim 15, wherein said primary arterial thrombotic complications of atherosclerosis are thrombotic stroke, peripheral vascular disease, or myocardial infarction without thrombolysis.

18. The method according to claim 15, wherein said thrombotic complications of interventions of atherosclerotic disease are associated with angioplasty, endarterectomy, stent placement, coronary or other vascular graft surgery.

19. The method according to claim 15, wherein said thrombotic complications of surgical or mechanical damage are associated with tissue salvage following surgical or accidental trauma, reconstructive surgery including skin flaps, or reductive surgery such as breast reduction.

20. The method according to claim 15, wherein said mechanically-induced platelet activation is caused by cardiopulmonary bypass resulting in microthromboembolism.

21. The method according to claim 15, wherein said shunt occlusion is renal dialysis or plasmapheresis.

22. The method according to claim 15, wherein said thrombosis secondary to vascular damage and inflammation is vasculitis, arteritis, glomerulonephritis or organ graft rejection.

23. The method according to claim 15, wherein said indications with a diffuse thrombotic/platelet consumption component are disseminated intravascular coagulation, thrombotic thrombocytopenic purpura, hemolytic uremic syndrome, heparin-induced thrombocytopenia, or pre-eclampsia/eclampsia.

24. The method according to claim 15, wherein said venous thrombosis is deep vein thrombosis, veno-occlusive disease, hematological conditions, or migraine.

25. The method according to claim 24, wherein said hematological conditions are thrombocythemia or polycythemia.

26. The method according to claim 15, wherein said coronary arterial thrombosis is associated with unstable angina, coronary angioplasty or acute myocardial infarction.

27. The method according to claim 15, wherein pathological effects of atherosclerosis and arteriosclerosis are arteriosclerosis, acute myocardial infarction, chronic stable angina, unstable angina, transient ischemic attacks, strokes, peripheral vascular disease, arterial thrombosis, preeclampsia, embolism, restenosis or abrupt closure following angioplasty, carotid endarterectomy, or anastomosis of vascular grafts.

28. The method according to claim 15, wherein said chronic or acute states of hyper-aggregability is caused by DIC, septicemia, surgical or infectious shock, post-operative and post-partum trauma, cardiopulmonary bypass surgery, incompatible blood transfusion, abruptio placenta, thrombotic thrombocytopenic purpura, snake venom or immune diseases.

29. The method according to claim 15, wherein said reocclusion of an artery or vein following fibrinolytic therapy is inhibited by internal administration of said compound with a fibrinolytic agent.

30. The method according to claim 29, wherein said fibrinolytic agent is selected from the group consisting of natural or synthetic products which directly or indirectly cause lysis of a fibrin clot.

31. The method according to claim 29, wherein said fibrinolytic agent is a plasminogen activator selected from the group consisting of anistreplase, urokinase, pro-urokinase, streptokinase, tissue plasminogen activator and mutants or variants thereof, which retain plasminogen activator activity.

32. The method according to claim 31, wherein said variants are selected from the group consisting of variants which have been chemically modified, variants which one or more amino acids have been added, deleted or substituted and variants with one or more modified functional domains.

33. The method according to claim 32, wherein said modified functional domains are added, deleted or altered by combining the active site of one plasminogen activator or fibrin binding domain with another plasminogen activator or fibrin binding molecule.

34. The pharmaceutical formulation according to claim 1, wherein said formulation is sterile.

35. The pharmaceutical formulation according to claim 1, wherein said formulation further comprises a pharmaceutical carrier.

36. The pharmaceutical formulation according to claim 1, wherein said formulation further comprises a buffering agent.

37. A compound of general formula I, or salts thereof:

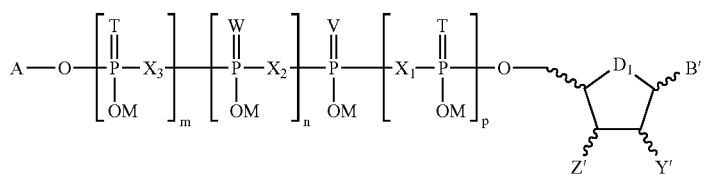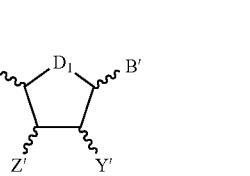

Formula I wherein:

$X_1$, $X_2$, and $X_3$ are independently selected from the group consisting of oxygen, methylene, monochloromethylene, dichloromethylene, monofluoromethylene, difluoromethylene, and imido;

T, W, and V are independently oxygen or sulfur;

m=0, 1 or 2;

n=0, 1, or 2;

p=0, 1, or 2;

M=H or a pharmaceutically-acceptable inorganic or organic counterion;

$D_1$=O or C;

B' is a purine or a pyrimidine residue according to general formulas IV and V which is linked to the 1' position of the furanose or carbocycle via the 9- or 1-position, respectively;

A is M or alkyl; or

A is a nucleoside residue which is defined as:

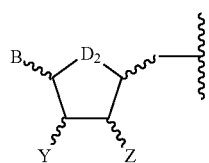

and which is linked to the phosphate chain via the 5' position of the furanose or carbocycle;

wherein:

$D_2$=O or C;

B is a purine or a pyrimidine residue according to general formulas IV and V which is linked to the sugar or carbocycle via the 9- or 1-position, respectively;

wherein when $D_1$ and $D_2$ are oxygen, the furanose is in the β-configuration;

Y'=H, OH, or $OR_1$, where $OR_1$ falls under the definition of general Formula II or III;

Z'=OH or $OR_2$, where $OR_2$ falls under the definition of general Formula II or III;

Z=OH or $OR_3$, where $OR_3$ falls under the definition of general Formula II or III;

Y=H, OH, or $OR_4$, where $OR_4$ falls under the definition of general Formula II or III;

provided that at least one of Y', Z', Z, and Y is $OR_1$, $OR_2$, $OR_3$, or $OR_4$, respectively;

wherein compounds of general Formula I are molecules whose structures fall within the definitions of Formula Ia and Formula Ib:

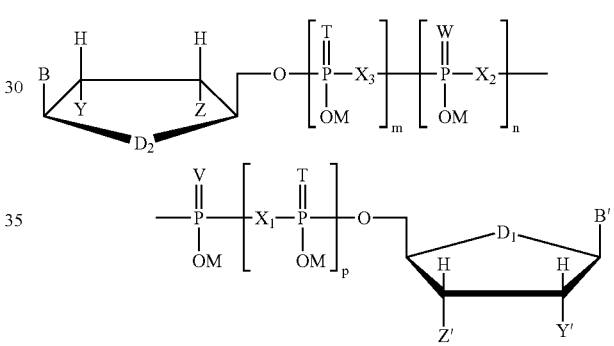

Formula Ia wherein:

$X_1$, $X_2$, and $X_3$=O;

T, V, and W=O;

M=H, $NH_4^+$, $Na^+$ or other pharmaceutically-acceptable inorganic or organic counterion;

Y'=H, OH, or $OR_1$, where $OR_1$ falls under the definition of general formula II;

Z'=OH or $OR_2$, where $OR_2$ falls under the definition of general formula II;

Z=OH or $OR_3$, where $OR_3$ falls under the definition of general formula II;

Y=H, OH, or $OR_4$, where $OR_4$ falls under the definition of general formula II;

provided that at least one of Y', Z', Z, and Y is $OR_1$, $OR_2$, $OR_3$, or $OR_4$, respectively;

$D_1$=O;

$D_2$=O or C;

B and B' are purine or pyrimidine residues according to general formulas IV and V;

m and p=0, 1 or 2;

n=0 or 1;

such that the sum of m+n+p is from 0 to 5; or $X_1$, $X_2$, and $X_3$=O;

T, V, and W=O;

M=H, $NH_4^+$, $Na^+$ or other pharmaceutically-acceptable inorganic or organic counterion;

$D_1$=O; Y'=H, OH, or $OR_1$, where $OR_1$ falls under the definition of general formula III;
Z'=OH or $OR_2$, where $OR_2$ falls under the definition of general formula III;
Z=OH or $OR_3$, where $OR_3$ falls under the definition of general formula III;
Y=H, OH, or $OR_4$, where $OR_4$ falls under the definition of general formula III;
provided that at least one of Y', Z', Z, and Y is $OR_1$, $OR_2$, $OR_3$, or $OR_4$, respectively;
$D_2$=O or C;
B and B' are purine or pyrimidine residues according to general formulas IV and V;
m and p=0, 1 or 2;
n=0 or 1;
such that the sum of m+n+p is from 0 to 5; or
$X_1$ and $X_3$=O;
$X_2$ is selected from the group consisting of methylene, monochloromethylene, dichloromethylene, monofluoromethylene, difluoromethylene, and imido;
T, V, and W=O;
M=H, $NH_4^+$, $Na^+$ or other pharmaceutically-acceptable inorganic or organic counterion;
Y'=H, OH, or $OR_1$, where $OR_1$ falls under the definition of general formula II;
Z'=OH or $OR_2$, where $OR_2$ falls under the definition of general formula II;
Z=OH or $OR_3$, where $OR_3$ falls under the definition of general formula II;
Y=H, OH, or $OR_4$, where $OR_4$ falls under the definition of general formula II;
provided that at least one of Y', Z', Z, and Y is $OR_1$, $OR_2$, $OR_3$, or $OR_4$, respectively;
$D_1$=O;
$D_2$=O or C;
B and B' are purine or pyrimidine residues according to general formulas IV and V;
m and p=0, 1 or 2;
n=1;
such that the sum of m+n+p is from 0 to 5; or
$X_1$ and $X_3$=O;
$X_2$ is selected from the group consisting of methylene, monochloromethylene, dichloromethylene, monofluoromethylene, difluoromethylene, and imido;
T, V, and W=O;
M=H, $NH_4^+$, $Na^+$ or other pharmaceutically-acceptable inorganic or organic counterion;
Y'=H, OH, or $OR_1$, where $OR_1$ falls under the definition of general formula III;
Z'=OH or $OR_2$, where $OR_2$ falls under the definition of general formula III;
Z=OH or $OR_3$, where $OR_3$ falls under the definition of general formula III;
Y=H, OH, or $OR_4$, where $OR_4$ falls under the definition of general formula III;
provided that at least one of Y', Z', Z, and Y is $OR_1$, $OR_2$, $OR_3$, or $OR_4$, respectively;
$D_1$=O;
$D_2$ is O or C;
B and B' are purine or pyrimidine residues according to general formulas IV and V;
m and p=0, 1 or 2;
n=1;
such that the sum of m+n+p is from 0 to 5; or
$X_1$ and $X_3$=O;
$X_2$ is selected from the group consisting of methylene, monochloromethylene, dichloromethylene, monofluoromethylene, difluoromethylene, and imido;
T=S;
V and W=O;
M=H, $NH_4^+$, $Na^+$ or other pharmaceutically-acceptable inorganic or organic counterion;
Y'=H, OH, or $OR_1$, where $OR_1$ falls under the definition of general formula II;
Z'=OH or $OR_2$, where $OR_2$ falls under the definition of general formula II;
Z=OH or $OR_3$, where $OR_3$ falls under the definition of general formula II;
Y=H, OH, or $OR_4$, where $OR_4$ falls under the definition of general formula II;
provided that at least one of Y', Z', Z, and Y is $OR_1$, $OR_2$, $OR_3$, or $OR_4$, respectively;
$D_1$=O;
$D_2$=O or C;
B and B' are purine or pyrimidine residues according to general formulas IV and V;
m, n and p=1; or
$X_1$ and $X_3$=O;
$X_2$ is selected from the group consisting of methylene, monochloromethylene, dichloromethylene, monofluoromethylene, difluoromethylene, and imido;
T=S;
V and W=O;
M is selected from the group consisting of H, $NH_4^+$, $Na^+$ and other pharmaceutically-acceptable inorganic or organic counterion;
Y'=H, OH, or $OR_1$, where $OR_1$ falls under the definition of general formula III;
Z'=OH or $OR_2$, where $OR_2$ falls under the definition of general formula III;
Z=OH or $OR_3$, where $OR_3$ falls under the definition of general formula III;
Y=H, OH, or $OR_4$, where $OR_4$ falls under the definition of general formula III;
provided that at least one of Y', Z', Z, and Y is $OR_1$, $OR_2$, $OR_3$, or $OR_4$, respectively;
$D_1$=O;
$D_2$=O or C;
B and B' are purine or pyrimidine residues according to general formulas IV and V;
m, n, and p=1;

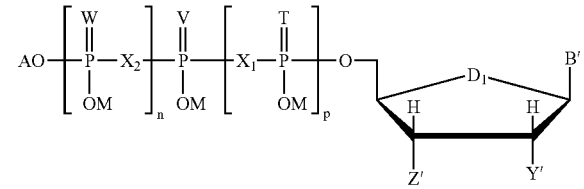

Formula Ib wherein:
A is M or alkyl;
$X_1$ and $X_2$=O;
T, V, and W=O;
M=H, $NH_4^+$, $Na^+$ or other pharmaceutically-acceptable inorganic or organic counterion;

Y'=H, OH, or OR$_1$, where OR$_1$ falls under the definition of general formula II;

Z'=H, OH or OR$_2$, where OR$_2$ falls under the definition of general formula II;

with the provision that at least one of Y' and Z' is OR$_1$ or OR$_2$;

D$_1$=O or C;

B' is purine or pyrimidine residue according to general formulas IV and V;

n and p are 0, 1, or 2 such that the sum of n+p is from 1 to 3; or

A is M or alkyl;

X$_1$ and X$_2$=O;

T, V, and W=O;

M is selected from the group consisting of H, NH$_4^+$, Na$^+$ and other pharmaceutically-acceptable inorganic or organic counterion;

Y'=OR$_1$, where OR$_1$ falls under the definition of general formula III;

Z'=OR$_2$, where OR$_2$ falls under the definition of general formula III;

D$_1$=O or C;

B' is purine or pyrimidine residue according to general formulas IV and V;

n and p are 0, 1, or 2 such that the sum of n+p is from 1 to 3; or

A is M or alkyl;

X$_1$ and X$_2$=O;

T and V=O;

W=S;

M=H, NH$_4^+$, Na$^+$ or other pharmaceutically-acceptable inorganic or organic counterion;

Y'=H, OH, or OR$_1$, where OR$_1$ falls under the definition of general formula II;

Z'=H, OH or OR$_2$, where OR$_2$ falls under the definition of general formula II;

with the provision that at least one of Y' and Z' is OR$_1$ or OR$_2$;

D$_1$=O or C;

B' is purine or pyrimidine residue according to general formulas IV and V;

p is 0, 1, or 2 such that the sum of n+p is from 1 to 3; n=1; or

A is M or alkyl;

X$_1$ and X$_2$=O;

T and V=O;

W=S;

M is selected from the group consisting of H, NH$_4^+$, Na$^+$ and other pharmaceutically-acceptable inorganic or organic counterion;

Y'=OR$_1$, where OR$_1$ falls under the definition of general formula III;

Z'=OR$_2$, where OR$_2$ falls under the definition of general formula III;

D$_1$=O or C;

B' is purine or pyrimidine residue according to general formulas IV and V;

p is 0, 1, or 2 such that the sum of n+p is from 1 to 3; n=1; or

A is M or alkyl;

X$_1$=O;

X$_2$ is selected from the group consisting of methylene, monochloromethylene, dichloromethylene, monofluoromethylene, difluoromethylene, and imido;

T, V, and W=O;

M is selected from the group consisting of H, NH$_4^+$, Na$^+$ and other pharmaceutically-acceptable inorganic or organic counterion;

Y'=H, OH, or OR$_1$, where OR$_1$ falls under the definition of general formula II;

Z'=H, OH or OR$_2$, where OR$_2$ falls under the definition of general formula II;

with the provision that at least one of Y' and Z' is OR$_1$ or OR$_2$;

D$_1$=O or C;

B' is purine or pyrimidine residue according to general formulas IV and V;

p is 0, 1, or 2 such that the sum of n+p is from 1 to 3; n=1; or

A is M or alkyl;

X$_1$=O;

X$_2$ is selected from the group consisting of methylene, monochloromethylene, dichloromethylene, monofluoromethylene, difluoromethylene, and imido;

T, V, and W=O;

M is selected from the group consisting of H, NH$_4^+$, Na$^+$ and other pharmaceutically-acceptable inorganic or organic counterion;

Y'=H, OH, or OR$_1$, where OR$_1$ falls under the definition of general formula III;

Z'=H, OH or OR$_2$, where OR$_2$ falls under the definition of general formula III;

D$_1$=O or C;

B' is purine or pyrimidine residue according to general formulas IV and V;

p is 0, 1, or 2 such that the sum of n+p is from 1 to 3; n=1;

wherein, for compounds according to Formula Ia or Ib, where Y'=OR$_1$, Z'=OR$_2$, Z=OR$_3$ and/or Y=OR$_4$, at least one of the four is a residue which is linked directly to the corresponding 2' or 3' hydroxyl oxygen of the furanose or carbocycle via a carbon atom; wherein said residue falls within the scope of formula II or formula III:

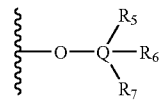

Formula II wherein:

O is the corresponding 2' or 3' oxygen of the furanose or carbocycle;

R$_5$, R$_6$, and R$_7$ are selected from the group consisting of H, an alkyl, cycloalkyl, aralkyl, aryl, substituted aralkyl, and substituted aryl, such that the moiety defined according to formula II is an ether; or R$_5$ and R$_6$ are taken together to be oxygen or sulfur doubly bonded to Q, and R$_7$ is selected from the group consisting of alkyl, cycloalkyl, aralkyl, aryl, substituted aralkyl, ad substituted aryl, such that the moiety defined according to formula II is an ester or thioester; or R$_5$ and R$_6$ are taken together to be oxygen or sulfur doubly bonded to Q, and R$_7$ is amino or mono- or disubstituted amino, where the substituents are selected from the group consisting of alkyl, cycloalkyl, aralkyl, aryl, substituted aralkyl, and substituted aryl, such that the moiety according to formula II is a carbamate or thiocarbamate; or R$_5$ and R$_6$ are taken together to be oxygen or sulfur doubly bonded to Q, and R$_7$ is selected from the group consisting of alkoxy, cycloalkoxy, aralkyloxy, aryloxy, substituted aralkyloxy, and substituted aryloxy, such that the moiety according to formula II is a carbonate or thiocarbonate; or R$_5$ and R$_6$ are taken together to be oxygen or sulfur doubly bonded to Q and both the 2' and 3' oxygens of the furanose are directly bound to Q to form a cyclical carbonate or thiocarbonate, R$_7$ is not present;

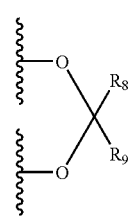

Formula III wherein:

O is the 2' and 3' oxygens of the furanose or carbocycle; and the 2' and 3' oxygens of the furanose or carbocycle are linked by a common carbon atom to form a cyclical acetal, cyclical ketal, or cyclical orthoester; and for cyclical acetals and ketals, R$_8$ and R$_9$ are independently selected from the group consisting of hydrogen, alkyl, cycloalkyl, aralkyl, aryl, substituted aralkyl, and substituted aryl; or are joined together to form a homocyclic or heterocyclic ring composed of 3 to 8 atoms, or for cyclical orthoesters, R$_8$ is selected from the group consisting of hydrogen, alkyl, cycloalkyl, aralkyl, aryl, substituted aralkyl, and substituted aryl, and R$_9$ is selected from the group consisting of alkyloxy, cycloalkyloxy, aralkyloxy, aryloxy, substituted aralkyloxy, and substituted aryloxy;

B and B' are independently a purine residue, as in formula IV, linked through the 9-position, or a pyrimidine residue, as in formula V, linked through the 1-position;

wherein, provided when D$_1$ and D$_2$ are oxygen, the ribosyl moieties are in the D-configuration;

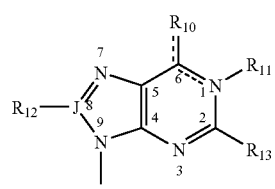

Formula IV

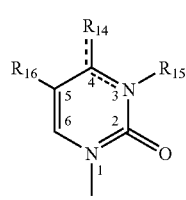

Formula V wherein:

R$_{10}$ and R$_{14}$ are selected from the group consisting of alkylthio, alkyloxy, aryloxy, cycloalkylamino, aralkylamino, arylamino, diaralkylamino, and diarylamino, where the alkyl groups are optionally linked to form a heterocycle; or R$_{10}$ and R$_{14}$ are acylamino according to Formula VI, provided that they incorporate an amino residue from the C-6 position of the purine or the C-4 position of the pyrimidine; or when R$_{10}$ in a purine or R$_{14}$ in a pyrimidine has as its first atom nitrogen, R$_{10}$ and R$_{11}$ or R$_{14}$ and R$_{15}$ are taken together to form a 5-membered fused imidazole ring, optionally substituted on the etheno ring with R$_5$–R$_9$ selected from the group consisting of alkyl, cycloalkyl, aralkyl, or aryl moieties, as described above;

J is carbon or nitrogen, with the provision that when nitrogen, R$_{12}$ is not present;

R$_{11}$ is hydrogen, O or is absent;

R$_{12}$ is selected from the group consisting of hydrogen, alkyl, azido, alkylamino, arylamino, aralkylamino, alkoxy, aryloxy, aralkyloxy, alkylthio, arythio, aralkylthio, and ω-A(C$_{1-6}$alkyl)B- wherein A and B are selected from the group consisting of independently amino, mercapto, hydroxy and carboxyl;

R$_{13}$ is selected from the group consisting of hydrogen, chlorine, amino, monosubstituted amino, disubstituted amino, alkylthio, arylthio, and aralkylthio, where the substituent on sulfur contains up to a maximum of 20 carbon atoms, with or without unsaturation;

R$_{15}$ is selected from the group consisting of hydrogen, and acyl, such as acetyl, benzoyl, phenylacyl, with or without substituents;

R$_{16}$ is selected from the group consisting of hydrogen, methyl, alkyl, halo, alkyl, alkenyl, substituted alkenyl, alkynyl, and substituted alkynyl;

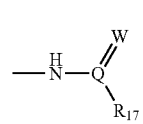

Formula VI wherein:

NH is the amino residue at the C-6 position in a purine or the amino residue at the C-4 position in a pyrimidine;

Q is a carbon atom;

W is oxygen or sulfur;

R$_{17}$ is amino or mono- or disubstituted amino such that the moiety according to formula VI is a urea or thiourea; or R$_{17}$ is selected from the group consisting of alkoxy, aralkyloxy, aryloxy, substituted aralkyloxy, and substituted aryloxy, such that the moiety according to formula VI is a carbamate or thiocarbamate; or R$_{17}$ is selected from the group consisting of alkyl, cycloalkyl, aralkyl, and aryl, with or without substituents or heteroatoms, such that the moiety according to formula VI is an amide.

38. The pharmaceutical formulation of claim 1 wherein said compound is a compound of Formula I:

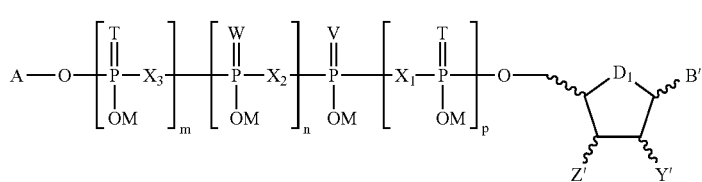

Formula I wherein:
V=O;
n=m=p=0;
A=M;
M=H or a pharmaceutically-acceptable inorganic or organic counterion;
$D_1$=O;

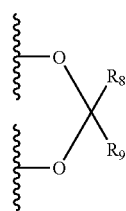

Formula III wherein:
O is the 2' and 3' oxygens of the furanose; and
the 2' and 3' oxygens of the furanose are linked by a common carbon atom to form a cyclical acetal; and
$R_8$ is hydrogen; and
$R_9$ is selected from the group consisting of aralkyl, aryl, substituted aralkyl, and substituted aryl;
in which the aralkyl groups are from 1 to 5 carbons in the alkyl portion, and are: monocyclic moieties from 4 to 8 carbons without heteroatoms in the aryl portion; and the aryl groups are monocyclic moieties from 4 to 8 carbons, without heteroatoms;
B' is a purine residue according to general Formula IV
wherein:

$R_{10}$ is acylamino, according to Formula VI;
W is oxygen; and
$R_{17}$ is amino or mono- or disubstituted amino such that the moiety according to Formula VI is a urea;
J=carbon;
$R_{11}$ is absent;
$R_{12}$ is hydrogen; and
$R_{13}$ is hydrogen.

\* \* \* \* \*

UNITED STATES PATENT AND TRADEMARK OFFICE
CERTIFICATE OF CORRECTION

| | | |
|---|---|---|
| PATENT NO. | : 7,018,985 B1 | Page 1 of 6 |
| APPLICATION NO. | : 09/643138 | |
| DATED | : March 28, 2006 | |
| INVENTOR(S) | : José L. Boyer et al. | |

It is certified that error appears in the above-identified patent and that said Letters Patent is hereby corrected as shown below:

Column 8, at line 66, change "n and p=0.1, or 2" to --n and p=0, 1, or 2--.

Column 9, at line 28, change "Z'=OH" to --Z'=H, OH,--.

Column 18, line 14, change "121.47 NHz" to --121.47 MHz--.

Column 19, line 53, change "(b 24mg" to --(24mg--.

Column 20, line 43, change "β - 10.13" to --δ -10.13--.

Column 20, line 53, change "β 4.10" to --δ 4.10--.

Column 25, line 13, Claim 1, after "thereof", insert --and a pharmaceutically acceptable carrier--.

Column 26, line 27, Claim 1, insert --wherein:-- before "$X_1$, $X_2$, and $X_3$ =O".

Column 27, line 32, Claim 1, change "0 to 5" to --1 to 5--.

Column 27, line 58, Claim 1, change "0 to 5" to --1 to 5--.

Column 28, lines 36-37, Claim 1, change "OR1, OR2, OR3, or OR4" to --$OR_1$, $OR_2$, $OR_3$, or $OR_4$--.

Column 29, lines 4-5, Claim 1, change "1 to 3" to --0 to 3--.

Column 29, lines 21-22, Claim 1, change "1 to 3" to --0 to 3--.

Column 30, line 51, Claim 1, before "alkyl", delete "an".

Column 31, line 67 through Column 32, line 2, Claim 1, delete "provided that they incorporate an amino residue from the C-6 position of the purine or the C-4 position of the pyrimidine;".

Column 32, line 8, Claim 1, delete ", as described above".

UNITED STATES PATENT AND TRADEMARK OFFICE
CERTIFICATE OF CORRECTION

| | | |
|---|---|---|
| PATENT NO. | : 7,018,985 B1 | |
| APPLICATION NO. | : 09/643138 | |
| DATED | : March 28, 2006 | |
| INVENTOR(S) | : José L. Boyer et al. | |

It is certified that error appears in the above-identified patent and that said Letters Patent is hereby corrected as shown below:

Column 32, line 14, Claim 1, change "aralkyloxy" to --aralkoxy--.

Column 32, lines 24-25, Claim 1, delete ", such as acetyl, benzoyl, phenylacyl, with or without substituents".

Column 32, line 27, Claim 1, delete "methyl, alkyl,".

Column 32, line 52, Claim 2, change "claim 1" to --claim 36--.

Column 33, line 24, Claim 10, change "a group" to --the group--.

Column 34, lines 11-12, Claim 19, delete "including skin flaps".

Column 34, line 12, Claim 19, delete "such as breast reduction".

Column 35, lines 8-10, Claim 35, delete "35. The pharmaceutical formulation according to claim 1, wherein said formulation further comprises a pharmaceutical carrier."

Column 35, line 11, renumber "36" to --35--.

Column 35, line 14, renumber "37" to --36--.

Column 37, line 43, change "0 to 5" to --1 to 5--.

Column 38, line 1, change "0 to 5" to --1 to 5--.

Column 39, lines 11-12, change "1 to 3" to --0 to 3--.

Column 39, lines 26-27, change "1 to 3" to --0 to 3--.

Column 40, line 58, change "aryl, substituted" to --and substituted--.

Column 40, line 59, delete "ad substituted aryl,".

Column 42, line 4, delete "alkylthio, alkyloxy,".

UNITED STATES PATENT AND TRADEMARK OFFICE
CERTIFICATE OF CORRECTION

PATENT NO. : 7,018,985 B1
APPLICATION NO. : 09/643138
DATED : March 28, 2006
INVENTOR(S) : José L. Boyer et al.

It is certified that error appears in the above-identified patent and that said Letters Patent is hereby corrected as shown below:

Column 42, lines 5-6, delete "aralkylamino, arylamino, diaralkylamino, and diarylamino,".

Column 42, line 6, before "where", insert --and dialkylamino--.

Column 42, lines 8-11, delete ", provided that they incorporate an amino residue from the C-6 position of the purine or the C-4 position of the pyrimidine".

Column 42, line 25, change "aralkyloxy" to --aralkoxy--.

Column 42, lines 35-36, delete ", such as acetyl, benzoyl, phenylacyl, with or without substituents".

Column 42, line 39, delete "methyl, alkyl,".

Column 42, line 66, renumber "38" to --37--.

Column 44, line 32, insert the following claims:

--38. The pharmaceutical formulation according to Claim 1, wherein said compound is Formula Ia, wherein $X_1$, $X_2$, and $X_3$=O;

T, V, and W= O;

M= H, $NH_4^+$, $Na^+$ or other pharmaceutically-acceptable inorganic or organic counterion;

Y'= H, OH, or $OR_1$, where $OR_1$ falls under the definition or general formula III;

Z'= OH or $OR_2$, where $OR_2$ falls under the definition of general formula III;

Z= OH or $OR_3$, where $OR_3$ falls under the definition of general formula III;

Y= H, OH, or $OR_4$ where $OR_4$ falls under the definition of general formula III;

UNITED STATES PATENT AND TRADEMARK OFFICE
CERTIFICATE OF CORRECTION

| | |
|---|---|
| PATENT NO. | : 7,018,985 B1 |
| APPLICATION NO. | : 09/643138 |
| DATED | : March 28, 2006 |
| INVENTOR(S) | : José L. Boyer et al. |

It is certified that error appears in the above-identified patent and that said Letters Patent is hereby corrected as shown below:

provided that at least one of Y', Z', Z, and Y is $OR_1$, $OR_2$, $OR_3$, or $OR_4$, respectively;

$D_1 = O$;

$D_2 = O$;

B and B' are purine or pyrimidine residues according to general formulas IV and V;

m and p= 0, 1 or 2;

n= 0 or 1.

such that the sum of m+n+p is from 0 to 5.

39.    The pharmaceutical formulation according to Claim 1, wherein said compound is Formula Ib, wherein A is M or alkyl;

$X_1$ and $X_2$= O;

T, V, and W= O;

M is selected from the group consisting of H, $NH_4^+$, $Na^+$ and other pharmaceutically-acceptable inorganic or organic counterion;

Y'= $OR_1$, where $OR_1$ falls under the definition of general formula III;

Z'= $OR_2$, where $OR_2$ falls under the definition of general formula III;

$D_1$ =O or C;

B' is purine or pyrimidine residue according to general formulas IV and V;

n and p are 0, 1, or 2 such that the sum of n+p is from 0 to 3.

UNITED STATES PATENT AND TRADEMARK OFFICE
CERTIFICATE OF CORRECTION

| | |
|---|---|
| PATENT NO. | : 7,018,985 B1 |
| APPLICATION NO. | : 09/643138 |
| DATED | : March 28, 2006 |
| INVENTOR(S) | : José L. Boyer et al. |

It is certified that error appears in the above-identified patent and that said Letters Patent is hereby corrected as shown below:

40. The pharmaceutical formulation according to Claim 1, wherein $R_{10}$ and $R_{14}$ are selected from the group consisting of aryloxy, cycloalkylamino, aralkylamino; and acylamino according to Formula VI;

J is carbon;

$R_{11}$ is absent;

$R_{12}$ is hydrogen, alkyl, alkylamino, aralkylamino, aralkoxy, or aralkylthio;

$R_{13}$ is hydrogen, chlorine, disubstituted amino, alkylthio, or aralkylthio;

$R_{15}$ is hydrogen; and $R_{16}$ is hydrogen, halo, or alkyl.

41. The method according to Claim 3, wherein said pharmaceutical formulation is a pharmaceutical formulation according to Claim 37.

42. The method according to Claim 3, wherein said pharmaceutical formulation is a pharmaceutical formulation according to Claim 38.

UNITED STATES PATENT AND TRADEMARK OFFICE
CERTIFICATE OF CORRECTION

| | |
|---|---|
| PATENT NO. | : 7,018,985 B1 |
| APPLICATION NO. | : 09/643138 |
| DATED | : March 28, 2006 |
| INVENTOR(S) | : José L. Boyer et al. |

It is certified that error appears in the above-identified patent and that said Letters Patent is hereby corrected as shown below:

43. The method according to Claim 3, wherein said pharmaceutical formulation is a pharmaceutical formulation according to Claim 39.

44. The method according to Claim 3, wherein said pharmaceutical formulation is a pharmaceutical formulation according to Claim 40. --

Signed and Sealed this

Third Day of June, 2008

JON W. DUDAS
*Director of the United States Patent and Trademark Office*